US007074599B2

(12) United States Patent
Uhl et al.

(10) Patent No.: US 7,074,599 B2
(45) Date of Patent: Jul. 11, 2006

(54) **DETECTION OF *MECA*-CONTAINING *STAPHYLOCOCCUS* SPP.**

(75) Inventors: James R. Uhl, Rochester, MN (US); Franklin R. Cockerill, III, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 127 days.

(21) Appl. No.: 10/261,083

(22) Filed: Sep. 27, 2002

(65) Prior Publication Data

US 2004/0063103 A1    Apr. 1, 2004

(51) Int. Cl.
*C12P 19/34* (2006.01)
*C12Q 1/68* (2006.01)
*C12N 1/00* (2006.01)
*C07H 21/04* (2006.01)

(52) U.S. Cl. .................. 435/91.2; 435/91.1; 435/6; 435/243; 536/23.1; 536/24.32; 536/24.33

(58) Field of Classification Search .............. 435/6, 435/91.2, 91.1, 243; 536/23.1, 24.3, 24.32, 536/24.33
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 4,800,159 A | 1/1989 | Mullis et al. | |
| 4,965,188 A | 10/1990 | Mullis et al. | |
| 4,996,143 A * | 2/1991 | Heller et al. ................ | 435/6 |
| 5,035,996 A * | 7/1991 | Hartley ...................... | 435/6 |
| 5,565,322 A | 10/1996 | Heller | |
| 5,683,896 A | 11/1997 | Hartley et al. | |
| 5,702,895 A * | 12/1997 | Matsunaga et al. ........ | 435/6 |
| 5,849,489 A | 12/1998 | Heller | |
| 5,945,313 A | 8/1999 | Hartley et al. | |
| 5,994,056 A * | 11/1999 | Higuchi ...................... | 435/6 |
| 6,001,564 A | 12/1999 | Bergeron et al. | |
| 6,162,603 A | 12/2000 | Heller | |

FOREIGN PATENT DOCUMENTS

| | | |
|---|---|---|
| EP | 269 764 | 6/1988 |
| EP | 0 526 876 | 2/1993 |
| EP | 1 045 033 | 10/2000 |
| EP | 1 160 333 A2 * | 5/2001 |
| EP | 1 160 333 | 12/2001 |
| WO | WO 92/05281 * | 4/1992 |
| WO | WO 97/46707 | 12/1997 |
| WO | WO 97/46712 | 12/1997 |
| WO | WO 97/46714 | 12/1997 |
| WO | WO 98/48046 | 10/1998 |
| WO | WO 99/19466 | 4/1999 |
| WO | WO 99/45155 | 9/1999 |
| WO | WO 01/12803 | 2/2001 |
| WO | WO 01/23604 | 4/2001 |
| WO | WO 02/18660 | 3/2002 |
| WO | WO 02/61390 | 8/2002 |
| WO | WO 03/068918 | 8/2003 |

OTHER PUBLICATIONS

Reischl et al. Rapid identification of Methicillin-resistant *Staphylococcus aureus* and simultaneous species confirmation using real-time fluorescence PCR. Journal of Clinical Microbiology, vol. 38, No. 6, pp. 2429-2433, Jun. 2000.*
Tan et al, Rapid identification of Methicillin-Resistant *Staphylococcus aures* from positive blood cultures by real-time fluorescence PCR. vol. 39, No. 12, p. 4529-4531, Dec. 2001.*
Grisold et al. Detection of Methicillin-Resistant *Staphylococcus aureus* and simultaneous confirmation by automated nucleic acid extraction and real-time PCR. Journal of clinical Microbiology, vol. 40, No. 7, pp. 2392-2397, Jul. 2002.*
Uhl et al. Detection of mecA genes in *Staphlococcus aures* and Coagulase-Negative *Staphylococcus* by a rapid PCR method. Abstract C-331, Abstracts of the general meeting of the American Society for Microbiology vol. 100, pp. 208, May 21-25, 2000.*
Buck et al. Design Strategies and performance of custom DNA sequencing primers. Biotechniques, vol. 27, No. 3, pp. 528-536, Sep. 1999.*
Reischl et al. Journal of Clinical Microbiology, vol. 38, No. 6, pp. 2429-2433, Jun. 2000.*
Grisold et al. Journal of Clinical Microbiology, vol. 40, No. 7, pp. 2392-2397, Jul. 2002.*
Tan et al. Journal of Clinical Microbiology, vol. 30, No. 12, pp. 4529-4531, Dec. 2001.*
GenBank Accession No. AB033763.
Geha et al., "Multiplex PCR for Identification of Methicillin-Resistant *Staphylococci* in the Clinical Laboratory," *J. Clin. Microbiol.*, 1994, 32(7):1768-1772.
Ito et al., "Structural Comparison of Three Types of Staphylococcal Cassette Chromosome *mec* Integrated in the Chromosome in Methicillin-Resistant *Staphylococcus aureus*," *Antimicrobial Agents and Chemotherapy*, 2001, 45(5):1323-1336.

(Continued)

*Primary Examiner*—Gary Benzion
*Assistant Examiner*—Cynthia Wilder
(74) *Attorney, Agent, or Firm*—Fish & Richardson P.C., P.A.

(57) ABSTRACT

The invention provides methods to detect mecA-containing *Staphylococcus* spp. in biological samples using real-time PCR. Primers and probes for the detection of *S. aureus* are provided by the invention. Articles of manufacture containing such primers and probes for detecting mecA-containing *Staphylococcus* spp. are further provided by the invention.

43 Claims, 4 Drawing Sheets

OTHER PUBLICATIONS

Bassler et al., "Use of a Fluorogenic Probe in a PCR-based Assay for the Detection of *Listeria monocytogenes*," *Applied and Environmental Microbiology*, 1995, 61(10):3724-3728.

Espy et al., "Diagnosis of Herpes Simplex Virus Infections in the Clinical Laboratory by LightCycler PCR," *J. Clin. Microbiol.*, 2000, 38(2):795-799.

Brink et al., "Nucleic Acid Sequence-Based Amplification, A New Method for Analysis of Spliced and Unspliced Epstein-Barr Virus Latent Transcripts, and Its Comparison with Reverse Transcriptase PCR," *J. Clin. Microbiol.*, 1998, 36(11):3164-3169.

Caplin et al., "LightCycler™ hybridization probes; The most direct way to monitor PCR amplification for quantification and mutation detection," *Biochemica*, 1999, 1:5-8.

Espy et al., "Quantification of Epstein-Barr Virus (EBV) Viral Load in Transplant Patients by LightCycler PCR," *Abstracts of the General Meeting of the American Society for Microbiology*, 101st General Meeting, May 20-24, 2001, 101:182, Abstract No. C-148.

Espy et al., "Diagnosis of Varicella-Zoster Virus Infections in the Clinical Laboratory by LightCycler PCR," *J. Clin. Microbiol.*, 2000, 38(9):3187-3189.

Espy et al., "Diagnosis of Herpes Simplex Virus Infections in the Clinical Laboratory by LightCycler PCR," *J. Clin. Microbiol.*, 2000, 38(2):795-799.

Espy et al., "Detection of Smallpox Virus DNA by LightCycler PCR," *J. Clin. Microbiol.*, 2002, 40(6):1985-1988.

Sample et al., "Two Related Epstein-Barr Virus Membrane Proteins are Encoded by Separate Genes," *J. Virol.*, 1989, 63(2):933-937.

Smith, "Application of Lightcycler Real Time PCR in Clinical Virology," *Clin. Chem. Lab. Med.*, 2001, Special Supplement, 39:S60, Abstract No. ISW14-2.

Telenti et al., "Detection of Epstein-Barr Virus by Polymerase Chain Reaction," *J. Clin. Microbiol.*, 1990, 28(10):2187-2190.

Al-Robaiy et al., "Rapid Competitive PCR Using Melting Curve Analysis for DNA Quantification," *BioTechniques*, 2001, 31:1382-1388.

Bélanger et al., "Rapid Detection of Shiga Toxin-Producing Bacteria in Feces by Multriplex PCR with Molecular Beacons on the Smart Cycler," *J. Clin. Microbiol.*, 2002, 40:1436-1440.

Bellin et al., "Rapid Detection of Enterohemorrhagic *Escherichia coli* by Real-Time PCR with Fluorescent Hybridization Probes," *J. Clin. Microbiol.*, 2001, 39:370-374.

Chen et al., An Automated Fluorescent PCR Method for Detection of Shiga Toxin-Producing *Escherichia coli* in Foods,: *Appl. Environ. Microbiol.*, 1998, 64:4210-4216.

Didenko, "DNA Probes Using Fluorescence Resonance Energy Transfer (FRET): Designs and Applications," *BioTechniques*, 2001, 31:1106-1121.

Ramotar et al., "Direct Detection of Verotoxin-Producing *Escherichia coli* in Stool Samples by PCR," *J. Clin. Microbiol.*, 1995, 33:519-524.

Livak et al., "Oligonucleotides with Fluorescent Dyes at Opposite Ends Provide A Quenched Probe System Useful for Detecting PCR Product and Nucleic Acid Hybridization," *Genome Research*, 1995, 4:357-362.

Ryncarz et al., "Development of a High-Throughput Quantitative Assay for Detecting Herpes Simplex Virus DNA in Clinical Samples," *J. Clin. Microbiol.*, 1999, 37:1941-1947.

Arthur et al., "*Enterococcus faecium* transposon Tn1546 transposase, resolvase, vanR, vanS, vanH, vanA, vanX, vanY and teicoplanin resistance protein (vanZ) genes, complete cds," 1993, database accession No. M97297.

Grisold et al., "Detection of Methicillin-Resistant *Staphylococcus aureus* and Simultaneous Confirmation by Automated Nucleic Acid Extraction and Real-Time PCR," *J. Clin. Microbiol.*, 2002,40:2392-2397.

Huletsky et al., "Rapid Detection of Vancomycin-Resistant Enterococci Directly from Rectal Swabs by Real-Time PCR Using the Smart Cycler," *Abstracts of the Interscience Conference on Antimicrobial Agents and Chemotherapy*, Chicago, Illinois, Sep. 22-25, 2001, 41:409 (Abstract K-1195).

Ito et al., "*Staphylococcus aureus* DNA, type-I staphylococcal cassette chromosome mec," 1999, database accession No. AB033763.

"LightCycler-FastStart DNA Master Hybridization Probes," 1999 Roche Diagnostics GmbH Technical Manual, retrieved from the internet on Feb. 6, 2004: http://www.roche-applied-science.com.

Palladino et al., "Real-time PCR for the rapid detection of vanA and vanB genes," *Diagnostic Microbiology and Infectious Disease*, 2003, 45:81-84.

Palladino et al., "Rapid Detection of *vanA* and *vanB* Genes Directly from Clinical Specimens and Enrichment Broths by Real-Time Multiplex PCR Assay," *J. Clin. Microbiol.*, 2003, 41:2483-2486.

Patel et al., "*Enterococcus faecalis* vancomycin resistance protein (vanB) gene, partial cds," 1997, database accession No. U72704.

Patel et al., "*Enterococcus faecium* vancomycin resistance protein B (vanB) gene, partial cds," 1997, database accession No. U94528.

Petrich et al., "Direct detection of *vanA* and *vanB* genes in clinical specimens for rapid identification of vancomycin resistant enterococci (VRE) using multiplex PCR," *Molecular and Cellular Probes*, 1999, 13:275-281.

Reischl et al., "Rapid Identification of Methicillin-Resistant *Staphylococcus aureus* and Simultaneous Species Confirmation Using Real-Time Fluorescence PCR, " *J. Clin. Microbiol.*, 2000, 38:2429-2433.

Sloan et al., "Evaluation of a Combined Lightcycler Assay for the Detection of vanA, vanB, and vanB-2/3 Genes in Enterococci," *Abstracts of the General Meeting of the American Society for Microbiology*, 2002, 102:143 (Abstract C-242).

* cited by examiner

```
ATG AAA AAG ATA AAA ATT GTT CCA CTT ATT TTA ATA GTT GTA GTT GTC GGG TTT GGT ATA
--- --- --- +-- --- --- -+- --- --- --+ --- --- --- +-- --- --- -+- --- --- --+  60
TAC TTT TTC TAT TTT TAA CAA GGT GAA TAA AAT TAT CAA CAT CAA CAG CCC AAA CCA TAT
Met Lys Lys Ile Lys Ile Val Pro Leu Ile Leu Ile Val Val Val Val Gly Phe Gly Ile

TAT TTT TAT GCT TCA AAA GAT AAA GAA ATT AAT AAT ACT ATT GAT GCA ATT GAA GAT AAA
--- --- --- +-- --- --- -+- --- --- --+ --- --- --- +-- --- --- -+- --- --- --+ 120
ATA AAA ATA CGA AGT TTT CTA TTT CTT TAA TTA TTA TGA TAA CTA CGT TAA CTT CTA TTT
Tyr Phe Tyr Ala Ser Lys Asp Lys Glu Ile Asn Asn Thr Ile Asp Ala Ile Glu Asp Lys

AAT TTC AAA CAA GTT TAT AAA GAT AGC AGT TAT ATT TCT AAA AGC GAT AAT GGT GAA GTA
--- --- --- +-- --- --- -+- --- --- --+ --- --- --- +-- --- --- -+- --- --- --+ 180
TTA AAG TTT GTT CAA ATA TTT CTA TCG TCA ATA TAA AGA TTT TCG CTA TTA CCA CTT CAT
Asn Phe Lys Gln Val Tyr Lys Asp Ser Ser Tyr Ile Ser Lys Ser Asp Asn Gly Glu Val

GAA ATG ACT GAA CGT CCG ATA AAA ATA TAT AAT AGT TTA GGC GTT AAA GAT ATA AAC ATT
--- --- --- +-- --- --- -+- --- --- --+ --- --- --- +-- --- --- -+- --- --- --+ 240
CTT TAC TGA CTT GCA GGC TAT TTT TAT ATA TTA TCA AAT CCG CAA TTT CTA TAT TTG TAA
Glu Met Thr Glu Arg Pro Ile Lys Ile Tyr Asn Ser Leu Gly Val Lys Asp Ile Asn Ile

CAG GAT CGT AAA ATA AAA AAA GTA TCT AAA AAT AAA AAA CGA GTA GAT GCT CAA TAT AAA
--- --- --- +-- --- --- -+- --- --- --+ --- --- --- +-- --- --- -+- --- --- --+ 300
GTC CTA GCA TTT TAT TTT TTT CAT AGA TTT TTA TTT TTT GCT CAT CTA CGA GTT ATA TTT
Gln Asp Arg Lys Ile Lys Lys Val Ser Lys Asn Lys Lys Arg Val Asp Ala Gln Tyr Lys

Mec449F
ATT AAA AC[AAC TAC GGT AAC ATT GAT CGG AAG] GTT CAA TTT AAT TTT GTT AAA GAA GAT
--- --- --- +-- --- --- -+- --- --- --+ --- --- --- +-- --- --- -+- --- --- --+ 360
TAA TTT TGT TTG ATG CCA TTG TAA CTA GCG TTG CAA GTT AAA TTA AAA CAA TTT CTT CTA
Ile Lys Thr Asn Tyr Gly Asn Ile Asp Arg Asn Val Gln Phe Asn Phe Val Lys Glu Asp

GGT ATG TGG AAG TTA GAT TGG GAT CAT AGC GTC ATT ATT CCA GGA ATG CAG AAA GAC CAA
--- --- --- +-- --- --- -+- --- --- --+ --- --- --- +-- --- --- -+- --- --- --+ 420
CCA TAC ACC TTC AAT CTA ACC CTA GTA TCG CAG TAA TAA GGT CCT TAC GTC TTT CTG GTT
Gly Met Trp Lys Leu Asp Trp Asp His Ser Val Ile Ile Pro Gly Met Gln Lys Asp Gln

AGC ATA CAT ATT GAA AAT TTA AAA TCA GAA CGT GGT AAA ATT TTA GAC CGA AAC AAT GTG
--- --- --- +-- --- --- -+- --- --- --+ --- --- --- +-- --- --- -+- --- --- --+ 480
TCG TAT GTA TAA CTT TTA AAT TTT AGT CTT GCA CCA TTT TAA AAT CTG GCT TTG TTA CAC
Ser Ile His Ile Glu Asn Leu Lys Ser Glu Arg Gly Lys Ile Leu Asp Arg Asn Asn Val mecHPF2                                    mecHPR2
GAA TTG GCC AAT ACA GGA ACA GCA TAT [                        ] TCT AAA
--- --- --- +-- --- --- -+- --- --- --+ --- --- --- +-- --- --- -+- --- --- --+ 540
CTT AAC CGG TTA TGT CCT TGT CGT ATA CTC TAT CCG TAG CAA GGT TTC TTA CAT AGA TTT
Glu Leu Ala Asn Thr Gly Thr Ala Tyr Glu Ile Gly Ile Val Pro Lys Asn Val Ser Lys AAA GAT TAT AAA GCA ATC GCT AAA GAA CTA AGT ATT TCT GAA GAC TAT ATC AAA CAA CAA
--- --- --- +-- --- --- -+- --- --- --+ --- --- --- +-- --- --- -+- --- --- --+ 600
TTT CTA ATA TTT CGT TAG CGA TTT CTT GAT TCA TAA AGA CTT CTG ATA TAG TTT GTT G[  ]
Lys Asp Tyr Lys Ala Ile Ala Lys Glu Leu Ser Ile Ser Glu Asp Tyr Ile Lys Gln Gln
```

Figure 1-1

```
ATG GAT CAA AAT TGG GTA CAA GAT GAT ACC TTC GTT CCA CTT AAA ACC GTT AAA AAA ATG
--- --- --- +-- --- --- -+- --- --- --+ --- --- --- +-- --- --- -+- --- --- --+ 660
TAC CTA GTT TTA ACC CAT CTA CTA CTA TGG AAG CAA GGT GAA TTT TGG CAA TTT TTT TAC
Met Asp Gln Asn Trp Val Gln Asp Asp Thr Phe Val Pro Leu Lys Thr Val Lys Lys Met
            Mec761R2

GAT GAA TAT TTA AGT GAT TTC GCA AAA AAA TTT CAT CTT ACA ACT AAT GAA ACA GAA AGT
--- --- --- +-- --- --- -+- --- --- --+ --- --- --- +-- --- --- -+- --- --- --+ 720
CTA CTT ATA AAT TCA CTA AAG CGT TTT TTT AAA GTA GAA TGT TGA TTA CTT TGT CTT TCA
Asp Glu Tyr Leu Ser Asp Phe Ala Lys Lys Phe His Leu Thr Thr Asn Glu Thr Glu Ser

CGT AAC TAT CCT CTA GAA AAA GCG ACT TCA CAT CTA TTA GGT TAT GTT GGT CCC ATT AAC
--- --- --- +-- --- --- -+- --- --- --+ --- --- --- +-- --- --- -+- --- --- --+ 780
GCA TTG ATA GGA GAT CTT TTT CGC TGA AGT GTA GAT AAT CCA ATA CAA CCA GGG TAA TTG
Arg Asn Tyr Pro Leu Glu Lys Ala Thr Ser His Leu Leu Gly Tyr Val Gly Pro Ile Asn

TCT GAA GAA TTA AAA CAA AAA GAA TAT AAA GGC TAT AAA GAT GAT GCA GTT ATT GGT AAA
--- --- --- +-- --- --- -+- --- --- --+ --- --- --- +-- --- --- -+- --- --- --+ 840
AGA CTT CTT AAT TTT GTT TTT CTT ATA TTT CCG ATA TTT CTA CTA CGT CAA TAA CCA TTT
Ser Glu Glu Leu Lys Gln Lys Glu Tyr Lys Gly Tyr Lys Asp Asp Ala Val Ile Gly Lys

AAG GGA CTC GAA AAA CTT TAC GAT AAA AAG CTC CAA CAT GAA GAT GGC TAT CGT GTC ACA
--- --- --- +-- --- --- -+- --- --- --+ --- --- --- +-- --- --- -+- --- --- --+ 900
TTC CCT GAG CTT TTT GAA ATG CTA TTT TTC GAG GTT GTA CTT CTA CCG ATA GCA CAG TGT
Lys Gly Leu Glu Lys Leu Tyr Asp Lys Lys Leu Gln His Glu Asp Gly Tyr Arg Val Thr

ATC GTT GAC GAT AAT AGC AAT ACA ATC GCA CAT ACA TTA ATA GAG AAA AAG AAA AAA GAT
--- --- --- +-- --- --- -+- --- --- --+ --- --- --- +-- --- --- -+- --- --- --+ 960
TAG CAA CTG CTA TTA TCG TTA TGT TAG CGT GTA TGT AAT TAT CTC TTT TTC TTT TTT CTA
Ile Val Asp Asp Asn Ser Asn Thr Ile Ala His Thr Leu Ile Glu Lys Lys Lys Lys Asp

GGC AAA GAT ATT CAA CTA ACT ATT GAT GCT AAA GTT CAA AAG AGT ATT TAT AAC AAC ATG
--- --- --- +-- --- --- -+- --- --- --+ --- --- --- +-- --- --- -+- --- --- --+ 1020
CCG TTT CTA TAA GTT GAT TGA TAA CTA CGA TTT CAA GTT TTC TCA TAA ATA TTG TTG TAC
Gly Lys Asp Ile Gln Leu Thr Ile Asp Ala Lys Val Gln Lys Ser Ile Tyr Asn Asn Met

AAA AAT GAT TAT GGC TCA GGT ACT GCT ATC CAC CCT CAA ACA GGT GAA TTA TTA GCA CTT
--- --- --- +-- --- --- -+- --- --- --+ --- --- --- +-- --- --- -+- --- --- --+ 1080
TTT TTA CTA ATA CCG AGT CCA TGA CGA TAG GTG GGA GTT TGT CCA CTT AAT AAT CGT GAA
Lys Asn Asp Tyr Gly Ser Gly Thr Ala Ile His Pro Gln Thr Gly Glu Leu Leu Ala Leu

GTA AGC ACA CCT TCA TAT GAC GTC TAT CCA TTT ATG TAT GGC ATG AGT AAC GAA GAA TAT
--- --- --- +-- --- --- -+- --- --- --+ --- --- --- +-- --- --- -+- --- --- --+ 1140
CAT TCG TGT GGA AGT ATA CTG CAG ATA GGT AAA TAC ATA CCG TAC TCA TTG CTT CTT ATA
Val Ser Thr Pro Ser Tyr Asp Val Tyr Pro Phe Met Tyr Gly Met Ser Asn Glu Glu Tyr

AAT AAA TTA ACC GAA GAT AAA AAA GAA CCT CTG CTC AAC AAG TTC CAG ATT ACA ACT TCA
--- --- --- +-- --- --- -+- --- --- --+ --- --- --- +-- --- --- -+- --- --- --+ 1200
TTA TTT AAT TGG CTT CTA TTT TTT CTT GGA GAC GAG TTG TTC AAG GTC TAA TGT TGA AGT
Asn Lys Leu Thr Glu Asp Lys Lys Glu Pro Leu Leu Asn Lys Phe Gln Ile Thr Thr Ser
```

Figure 1-2

```
CCA GGT TCA ACT CAA AAA ATA TTA ACA GCA ATG ATT GGG TTA AAT AAC AAA ACA TTA GAC
--- --- --- +-- --- --- -+- --- --- --+ --- --- --- +-- --- --- -+- --- --- --+ 1260
GGT CCA AGT TGA GTT TTT TAT AAT TGT CGT TAC TAA CCC AAT TTA TTG TTT TGT AAT CTG
Pro Gly Ser Thr Gln Lys Ile Leu Thr Ala Met Ile Gly Leu Asn Asn Lys Thr Leu Asp

GAT AAA ACA AGT TAT AAA ATC GAT GGT AAA GGT TGG CAA AAA GAT AAA TCT TGG GGT GGT
--- --- --- +-- --- --- -+- --- --- --+ --- --- --- +-- --- --- -+- --- --- --+ 1320
CTA TTT TGT TCA ATA TTT TAG CTA CCA TTT CCA ACC GTT TTT CTA TTT AGA ACC CCA CCA
Asp Lys Thr Ser Tyr Lys Ile Asp Gly Lys Gly Trp Gln Lys Asp Lys Ser Trp Gly Gly

TAC AAC GTT ACA AGA TAT GAA GTG GTA AAT GGT AAT ATC GAC TTA AAA CAA GCA ATA GAA
--- --- --- +-- --- --- -+- --- --- --+ --- --- --- +-- --- --- -+- --- --- --+ 1380
ATG TTG CAA TGT TCT ATA CTT CAC CAT TTA CCA TTA TAG CTG AAT TTT GTT CGT TAT CTT
Tyr Asn Val Thr Arg Tyr Glu Val Val Asn Gly Asn Ile Asp Leu Lys Gln Ala Ile Glu

TCA TCA GAT AAC ATT TTC TTT GCT AGA GTA GCA CTC GAA TTA GGC AGT AAG AAA TTT GAA
--- --- --- +-- --- --- -+- --- --- --+ --- --- --- +-- --- --- -+- --- --- --+ 1440
AGT AGT CTA TTG TAA AAG AAA CGA TCT CAT CGT GAG CTT AAT CCG TCA TTC TTT AAA CTT
Ser Ser Asp Asn Ile Phe Phe Ala Arg Val Ala Leu Glu Leu Gly Ser Lys Lys Phe Glu

AAA GGC ATG AAA AAA CTA GGT GTT GGT GAA GAT ATA CCA AGT GAT TAT CCA TTT TAT AAT
--- --- --- +-- --- --- -+- --- --- --+ --- --- --- +-- --- --- -+- --- --- --+ 1500
TTT CCG TAC TTT TTT GAT CCA CAA CCA CTT CTA TAT GGT TCA CTA ATA GGT AAA ATA TTA
Lys Gly Met Lys Lys Leu Gly Val Gly Glu Asp Ile Pro Ser Asp Tyr Pro Phe Tyr Asn

GCT CAA ATT TCA AAC AAA AAT TTA GAT AAT GAA ATA TTA TTA GCT GAT TCA GGT TAC GGA
--- --- --- +-- --- --- -+- --- --- --+ --- --- --- +-- --- --- -+- --- --- --+ 1560
CGA GTT TAA AGT TTG TTT TTA AAT CTA TTA CTT TAT AAT AAT CGA CTA AGT CCA ATG CCT
Ala Gln Ile Ser Asn Lys Asn Leu Asp Asn Glu Ile Leu Leu Ala Asp Ser Gly Tyr Gly

CAA GGT GAA ATA CTG ATT AAC CCA GTA CAG ATC CTT TCA ATC TAT AGC GCA TTA GAA AAT
--- --- --- +-- --- --- -+- --- --- --+ --- --- --- +-- --- --- -+- --- --- --+ 1620
GTT CCA CTT TAT GAC TAA TTG GGT CAT GTC TAG GAA AGT TAG ATA TCG CGT AAT CTT TTA
Gln Gly Glu Ile Leu Ile Asn Pro Val Gln Ile Leu Ser Ile Tyr Ser Ala Leu Glu Asn

AAT GGC AAT ATT AAC GCA CCT CAC TTA TTA AAA GAC ACG AAA AAC AAA GTT TGG AAG AAA
--- --- --- +-- --- --- -+- --- --- --+ --- --- --- +-- --- --- -+- --- --- --+ 1680
TTA CCG TTA TAA TTG CGT GGA GTG AAT AAT TTT CTG TGC TTT TTG TTT CAA ACC TTC TTT
Asn Gly Asn Ile Asn Ala Pro His Leu Leu Lys Asp Thr Lys Asn Lys Val Trp Lys Lys

AAT ATT ATT TCC AAA GAA AAT ATC AAT CTA TTA ACT GAT GGT ATG CAA CAA GTC GTA AAT
--- --- --- +-- --- --- -+- --- --- --+ --- --- --- +-- --- --- -+- --- --- --+ 1740
TTA TAA TAA AGG TTT CTT TTA TAG TTA GAT AAT TGA CTA CCA TAC GTT GTT CAG CAT TTA
Asn Ile Ile Ser Lys Glu Asn Ile Asn Leu Leu Thr Asp Gly Met Gln Gln Val Val Asn

AAA ACA CAT AAA GAA GAT ATT TAT AGA TCT TAT GCA AAC TTA ATT GGC AAA TCC GGT ACT
--- --- --- +-- --- --- -+- --- --- --+ --- --- --- +-- --- --- -+- --- --- --+ 1800
TTT TGT GTA TTT CTT CTA TAA ATA TCT AGA ATA CGT TTG AAT TAA CCG TTT AGG CCA TGA
Lys Thr His Lys Glu Asp Ile Tyr Arg Ser Tyr Ala Asn Leu Ile Gly Lys Ser Gly Thr
```

Figure 1-3

```
GCA GAA CTC AAA ATG AAA CAA GGA GAA ACT GGC AGA CAA ATT GGG TGG TTT ATA TCA TAT
--- --- --- +-- --- --- -+- --- --- --+ --- --- --- +-- --- --- -+- --- --- --+ 1860
CGT CTT GAG TTT TAC TTT GTT CCT CTT TGA CCG TCT GTT TAA CCC ACC AAA TAT AGT ATA
Ala Glu Leu Lys Met Lys Gln Gly Glu Thr Gly Arg Gln Ile Gly Trp Phe Ile Ser Tyr

GAT AAA GAT AAT CCA AAC ATG ATG ATG GCT ATT AAT GTT AAA GAT GTA CAA GAT AAA GGA
--- --- --- +-- --- --- -+- --- --- --+ --- --- --- +-- --- --- -+- --- --- --+ 1920
CTA TTT CTA TTA GGT TTG TAC TAC TAC CGA TAA TTA CAA TTT CTA CAT GTT CTA TTT CCT
Asp Lys Asp Asn Pro Asn Met Met Met Ala Ile Asn Val Lys Asp Val Gln Asp Lys Gly

ATG GCT AGC TAC AAT GCC AAA ATC TCA GGT AAA GTG TAT GAT GAG CTA TAT GAG AAC GGT
--- --- --- +-- --- --- -+- --- --- --+ --- --- --- +-- --- --- -+- --- --- --+ 1980
TAC CGA TCG ATG TTA CGG TTT TAG AGT CCA TTT CAC ATA CTA CTC GAT ATA CTC TTG CCA
Met Ala Ser Tyr Asn Ala Lys Ile Ser Gly Lys Val Tyr Asp Glu Leu Tyr Glu Asn Gly

AAT AAA AAA TAC GAT ATA GAT GAA TAA
--- --- --- +-- --- --- -+- --- --- 2007
TTA TTT TTT ATG CTA TAT CTA CTT ATT
Asn Lys Lys Tyr Asp Ile Asp Glu ***
```

Figure 1-4

DETECTION OF *MECA*-CONTAINING *STAPHYLOCOCCUS* SPP.

TECHNICAL FIELD

This invention relates to bacterial diagnostics, and more particularly to detection of *Staphylococcus* spp. that contain mecA nucleic acid sequences.

BACKGROUND

Methicillin resistance in *Staphylococcus aureus* and coagulase-negative *staphylococcus* (CoNS) is associated with the presence of the mecA gene (Geha et al., 1994, *J. Clin. Microbiol.*, 32:1768). Isolates of *staphylococcus* that carry the mecA gene produce a modified penicillin-binding protein, PBP-2', which confers high-level resistance to all beta-lactams, including penicillins, semisynthetic penicillinase-resistant congeners, penems, carbapenems, and cephalosporins. Isolates of *staphylococcus* that are mecA positive should be considered resistant to all β-lactam antimicrobials.

SUMMARY

The invention provides for methods of identifying mecA-containing *Staphylococcus* spp. in a biological sample. Primers and probes for detecting mecA-containing *Staphylococcus* spp. are provided by the invention, as are kits containing such primers and probes. Methods of the invention can be used to rapidly detect the presence or absence of mecA-containing *Staphylococcus* spp. from specimens for diagnosis of *Staphylococcus* infection. Using specific primers and probes, the methods of the invention include amplifying and monitoring the development of specific amplification products using fluorescence resonance energy transfer (FRET).

In one aspect of the invention, there is provided a method for detecting the presence or absence of one or more mecA-containing *Staphylococcus* spp. in a biological sample from an individual. The method to detect mecA-containing *Staphylococcus* spp. includes performing at least one cycling step, which includes an amplifying step and a hybridizing step. The amplifying step includes contacting the sample with a pair of mecA primers to produce a mecA amplification product if a mecA nucleic acid molecule is present in the sample. The hybridizing step includes contacting the sample with a pair of mecA probes. Generally, the members of the pair of mecA probes hybridize within no more than five nucleotides of each other. A first mecA probe of the pair of mecA probes is typically labeled with a donor fluorescent moiety and a second mecA probe of the pair of mecA probes is labeled with a corresponding acceptor fluorescent moiety. The method further includes detecting the presence or absence of FRET between the donor fluorescent moiety of the first mecA probe and the acceptor fluorescent moiety of the second mecA probe. The presence of FRET is usually indicative of the presence of one or more mecA-containing *Staphylococcus* spp. in the sample, while the absence of FRET is usually indicative of the absence of a mecA-containing *Staphylococcus* spp. in the sample.

A pair of mecA primers generally includes a first mecA primer and a second mecA primer. A first mecA primer can include the sequence 5'-AAA CTA CGG TAA CAT TGA TCG CAA C-3' (SEQ ID NO:1), and a second mecA primer can include the sequence 5'-TCT TGT ACC CAA TTT TGA TCC ATT T-3' (SEQ ID NO:2). A first mecA probe can include the sequence 5'-GTG GAA TTG GCC AAT ACA GGA ACA GCA TA-3' (SEQ ID NO:3), and a second mecA probe can include the sequence 5'-GAG ATA GGC ATC GTT CCA AAG AAT GTA-3' (SEQ ID NO:4).

In some aspects, one of the mecA primers can be labeled with a fluorescent moiety (either a donor or acceptor, as appropriate) and can take the place of one of the mecA probes.

The members of the pair of mecA probes can hybridize within no more than two nucleotides of each other, or can hybridize within no more than one nucleotide of each other. A representative donor fluorescent moiety is fluorescein, and corresponding acceptor fluorescent moieties include LC™-RED 640 (LightCycler™-Red 640-N-hydroxysuccinimide ester), LC™-RED 705 (LightCycler™-Red 705-Phosphoramidite), and cyanine dyes such as CY5 and CY5.5. Additional corresponding donor and acceptor fluorescent moieties are known in the art.

In one aspect, the detecting step includes exciting the sample at a wavelength absorbed by the donor fluorescent moiety and visualizing and/or measuring the wavelength emitted by the acceptor fluorescent moiety (i.e., visualizing and'/or measuring FRET). In another aspect, the detecting step includes quantitating the FRET. In yet another aspect, the detecting step can be performed after each cycling step (e.g., in real-time).

Generally, the presence of FRET within 45 cycles (e.g., 20, 25, 30, 35, or 40 cycles) indicates the presence of a *Staphylococcus* infection in the individual. In addition, determining the melting temperature between one or both of the mecA probe(s) and the mecA amplification product can confirm the presence or absence of a mecA-containing *Staphylococcus* spp.

Representative biological sample include nasal swabs, throat swabs, feces, dermal swabs, lymphoid tissue, cerebrospinal fluid, blood (and blood in blood culture bottles), sputum, bronchio-alveolar lavage, bronchial aspirates, lung tissue, and urine. The above-described methods can further include preventing amplification of a contaminant nucleic acid. Preventing amplification can include performing the amplifying step in the presence of uracil and treating the sample with uracil-DNA glycosylase prior to amplifying.

In addition, the cycling step can be performed on a control sample. A control sample can include the same portion of the mecA nucleic acid molecule. Alternatively, a control sample can include a nucleic acid molecule other than a mecA nucleic acid molecule. Cycling steps can be performed on such a control sample using a pair of control primers and a pair of control probes. The control primers and probes are other than mecA primers and probes. One or more amplifying steps produces a control amplification product. Each of the control probes hybridizes to the control amplification product.

In another aspect of the invention, there are provided articles of manufacture, or kits. Kits of the invention can include a pair of mecA primers, and a pair of mecA probes, and a donor and corresponding acceptor fluorescent moieties. For example, the first mecA primer provided in a kit of the invention can have the sequence 5'-AAA CTA CGG TAA CAT TGA TCG CAA C-3' (SEQ ID NO:1) and the second mecA primer can have the sequence 5'-TCT TGT ACC CAA TTT TGA TCC ATT T-3' (SEQ ID NO:2). The first mecA probe provided in a kit of the invention can have the sequence 5'-GTG GAA TTG GCC AAT ACA GGA ACA GCA TA-3' (SEQ ID NO:3) and the second mecA probe can have the sequence 5'-GAG ATA GGC ATC GTT CCA AAG AAT GT-3' (SEQ ID NO:4).

Articles of manufacture can include fluorophoric moieties for labeling the probes or the probes can be already labeled with donor and corresponding acceptor fluorescent moieties. The article of manufacture can also include a package insert having instructions thereon for using the primers, probes, and fluorophoric moieties to detect the presence or absence of mecA-containing *Staphylococcus* spp. in a sample.

In yet another aspect of the invention, there is provided a method for detecting the presence or absence of mecA-containing *Staphylococcus* spp. in a biological sample from an individual. Such a method includes performing at least one cycling step. A cycling step can include an amplifying step and a hybridizing step. Generally, an amplifying step includes contacting the sample with a pair of mecA primers to produce a mecA amplification product if a mecA nucleic acid molecule is present in the sample. Generally, a hybridizing step includes contacting the sample with a mecA probe. Such a mecA probe is usually labeled with a donor fluorescent moiety and a corresponding acceptor fluorescent moiety. The method further includes detecting the presence or absence of fluorescence resonance energy transfer (FRET) between the donor fluorescent moiety and the acceptor fluorescent moiety of the mecA probe. The presence or absence of fluorescence is indicative of the presence or absence of mecA-containing *Staphylococcus* spp. in said sample.

In one aspect, amplification can employ a polymerase enzyme having 5' to 3'exonuclease activity. Thus, the first and second fluorescent moieties would be within no more than 5 nucleotides of each other along the length of the probe. In another aspect, the mecA probe includes a nucleic acid sequence that permits secondary structure formation. Such secondary structure formation generally results in spatial proximity between the first and second fluorescent moiety. According to this method, the second fluorescent moiety on a probe can be a quencher.

In another aspect of the invention, there is provided a method for detecting the presence or absence of mecA-containing *Staphylococcus* spp. in a biological sample from an individual. Such a method includes performing at least one cycling step. A cycling step can include an amplifying step and a dye-binding step. An amplifying step generally includes contacting the sample with a pair of mecA primers to produce a mecA amplification product if a mecA nucleic acid molecule is present in the sample. A dye-binding step generally includes contacting the mecA amplification product with a double-stranded DNA binding dye. The method further includes detecting the presence or absence of binding of the double-stranded DNA binding dye into the amplification product. According to the invention, the presence of binding is typically indicative of the presence of one or more mecA-containing *Staphylococcus* spp. in the sample, and the absence of binding is typically indicative of the absence of a mecA-containing *Staphylococcus* spp. in the sample. Such a method can further include the steps of determining the melting temperature between the mecA amplification product and the double-stranded DNA binding dye. Generally, the melting temperature confirms the presence or absence of mecA-containing *Staphylococcus* spp. Representative nucleic acid binding dyes include SYBRGREENI®, SYBRGOLD®, and ethidium bromide.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In addition, the materials, methods, and examples are illustrative only and not intended to be limiting. All publications, patent applications, patents, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the drawings and detailed description, and from the claims.

DESCRIPTION OF DRAWINGS

FIG. 1 shows the coding sequence of *Staphylococcus* mecA. Like reference symbols in the various drawings indicate like elements.

DETAILED DESCRIPTION

A real-time assay for detecting mecA-containing *Staphylococcus* spp. in a biological sample that is more sensitive and specific than existing assays is described herein. The invention provides primers and probes for detecting mecA-containing *Staphylococcus* spp. and articles of manufacture containing such primers and probes. The increased sensitivity of real-time PCR for detection of mecA-containing *Staphylococcus* spp. compared to other methods, as well as the improved features of real-time PCR including sample containment and real-time detection of the amplified product, make feasible the implementation of this technology for routine diagnosis of *Staphylococcus* infections in the clinical laboratory.

The assay described herein decreases the time it takes to detect methicillin resistance in *staphylococcus* from 2 to 3 days down to a few hours by utilizing sensitive and rapid PCR and specific FRET probe detection technology in a real-time PCR format. The assay provides the patient and physician with more rapid antibiotic susceptibility information necessary for appropriate treatment of infections. Methods of the invention can be used for rapid detection of the mecA gene associated resistance in isolates of *S. aureus* and CoNS. For isolates of *S. lugdunensis, S. cohnii, S. saprophyticus, S. warneri, S. xylosus*, the assay described herein may represent the most accurate means for determination of mecA-associated antibiotic resistance.

mecA Nucleic Acids and Oligonucleotides

The invention provides methods to detect mecA-containing *Staphylococcus* spp. by amplifying, for example, a portion of the mecA nucleic acid. mecA nucleic acid sequences other than those exemplified herein also can be used to detect mecA-containing *Staphylococcus* spp. in a sample and are known to those of skill in the art. The nucleic acid sequence of mecA is available (see, for example, GenBank Accession No. AB033763). The mecA sequence from 5 methicillin resistant *S. aureus* (MRSA) isolates and 5 methicillin resistant CoNS (MRCONS) isolates are identical to the mecA sequence from S. aureus. Homologs to mecA having approximately 80% homology are found in several *Staphylococcus* species (Ito et al., 2001, *Antimicrobial Agents and Chemotherapy*, 45:1323–36). Such homologous mecA sequences are not detecting using the primers and probes disclosed herein. Primers and probes can be designed, however, that would detect such mecA homologs.

Specifically, primers and probes to amplify and detect mecA nucleic acid molecules are provided by the invention.

Primers that amplify a mecA nucleic acid molecule, e.g., *S. aureus* mecA, can be designed using, for example, a computer program such as OLIGO (Molecular Biology Insights, Inc., Cascade, CO). Important features when designing oligonucleotides to be used as amplification primers include, but are not limited to, an appropriate size amplification product to facilitate detection (e.g., by electrophoresis), similar melting temperatures for the members of a pair of primers, and the length of each primer (i.e., the primers need to be long enough to anneal with sequence-specificity and to initiate synthesis but not so long that fidelity is reduced during oligonucleotide synthesis). Typically, oligonucleotide primers are 15 to 30 nucleotides in length. As used herein, "mecA primers" refers to oligonucleotide primers that anneal specifically to mecA nucleic acid sequences and initiate synthesis therefrom under appropriate conditions.

Designing oligonucleotides to be used as hybridization probes can be performed in a manner similar to the design of primers, although the members of a pair of probes preferably anneal to an amplification product within no more than 5 nucleotides of each other on the same strand such that FRET can occur (e.g., within no more than 1, 2, 3, or 4 nucleotides of each other). This minimal degree of separation typically brings the respective fluorescent moieties into sufficient proximity such that FRET occurs. It is to be understood, however, that other separation distances (e.g., 6 or more nucleotides) are possible provided the fluorescent moieties are appropriately positioned relative to each other (for example, with a linker arm) such that FRET can occur. In addition, probes can be designed to hybridize to targets that contain a polymorphism or mutation, thereby allowing differential detection of mecA-containing *Staphylococcus* spp. or isolate based on either absolute hybridization of different pairs of probes corresponding to the particular mecA-containing *Staphylococcus* spp. or isolate to be distinguished or differential melting temperatures between, for example, members of a pair of probes and each amplification product corresponding to a mecA-containing *Staphylococcus* spp. or isolate to be distinguished. As with oligonucleotide primers, oligonucleotide probes usually have similar melting temperatures, and the length of each probe must be sufficient for sequence-specific hybridization to occur but not so long that fidelity is reduced during synthesis. Oligonucleotide probes are generally 15 to 30 nucleotides in length. As used herein, "meca probes" refers to oligonucleotide probes that specifically anneal to meca amplification products.

Constructs of the invention include vectors containing a mecA nucleic acid molecule, e.g., *S. aureus* mecA, or a fragment thereof. Constructs of the invention can be used, for example, as control template nucleic acid molecules. Vectors suitable for use in the present invention are commercially available and/or produced by recombinant DNA technology methods routine in the art. mecA nucleic acid molecules can be obtained, for example, by chemical synthesis, direct cloning from a mecA-containing *Staphylococcus* spp., or by PCR amplification. A mecA nucleic acid molecule or fragment thereof can be operably linked to a promoter or other regulatory element such as an enhancer sequence, a response element, or an inducible element that modulates expression of the mecA nucleic acid molecule. As used herein, operably linking refers to connecting a promoter and/or other regulatory elements to a mecA nucleic acid molecule in such a way as to permit and/or regulate expression of the mecA nucleic acid molecule. A promoter that does not normally direct expression of mecA can be used to direct transcription of a mecA nucleic acid using, for example, a viral polymerase, a bacterial polymerase, or a eukaryotic RNA polymerase II. Alternatively, the mecA native promoter can be used to direct transcription of a mecA nucleic acid, respectively, using, for example, an RNA polymerase enzyme (e.g., RNA polymerase II). In addition, operably linked can refer to an appropriate connection between a mecA promoter or regulatory element and a heterologous coding sequence (i.e., a non-mecA coding sequence, for example, a reporter gene) in such a way as to permit expression of the heterologous coding sequence.

Constructs suitable for use in the methods of the invention typically include, in addition to mecA nucleic acid molecules, sequences encoding a selectable marker (e.g., an antibiotic resistance gene) for selecting desired constructs and/or transformants, and an origin of replication. The choice of vector systems usually depends upon several factors, including, but not limited to, the choice of host cells, replication efficiency, selectability, inducibility, and the ease of recovery.

Constructs of the invention containing mecA nucleic acid molecules can be propagated in a host cell. As used herein, the term host cell is meant to include prokaryotes and eukaryotes. Prokaryotic hosts may include *E. coli*, *Salmonella typhimurium*, *Serratia marcescens* and *Bacillus subtilis*. Eukaryotic hosts include yeasts such as *S. cerevisiae*, *S. pombe*, *Pichia pastoris*, mammalian cells such as COS cells or Chinese hamster ovary (CHO) cells, insect cells, and plant cells such as *Arabidopsis thaliana* and *Nicotiana tabacum*. A construct of the invention can be introduced into a host cell using any of the techniques commonly known to those of ordinary skill in the art. For example, calcium phosphate precipitation, electroporation, heat shock, lipofection, microinjection, and viral-mediated nucleic acid transfer are common methods for introducing nucleic acids into host cells. In addition, naked DNA can be delivered directly to cells (see, e.g., U.S. Pat. Nos. 5,580,859 and 5,589,466).

Polymerase Chain Reaction (PCR)

U.S. Pat. Nos. 4,683,202, 4,683,195, 4,800,159, and 4,965,188 disclose conventional PCR techniques. PCR typically employs two oligonucleotide primers that bind to a selected nucleic acid template (e.g., DNA or RNA). Primers useful in the present invention include oligonucleotide primers capable of acting as a point of initiation of nucleic acid synthesis within mecA sequences. A primer can be purified from a restriction digest by conventional methods, or it can be produced synthetically. The primer is preferably single-stranded for maximum efficiency in amplification, but the primer can be double-stranded. Double-stranded primers are first denatured, i.e., treated to separate the strands. One method of denaturing double stranded nucleic acids is by heating.

The term "thermostable polymerase" refers to a polymerase enzyme that is heat stable, i.e., the enzyme catalyzes the formation of primer extension products complementary to a template and does not irreversibly denature when subjected to the elevated temperatures for the time necessary to effect denaturation of double-stranded template nucleic acids. Generally, the synthesis is initiated at the 3' end of each primer and proceeds in the 5' to 3' direction along the template strand. Thermostable polymerases have been isolated from *Thermus flavus*, *T. ruber*, *T. thermophilus*, *T aquaticus*, *T. lacteus*, *T. rubens*, *Bacillus stearothermophilus*, and *Methanothermus fervidus*. Nonetheless, polymerases that are not thermostable also can be employed in PCR assays provided the enzyme is replenished.

If the *Staphylococcus* template nucleic acid is double-stranded, it is necessary to separate the two strands before it can be used as a template in PCR. Strand separation can be accomplished by any suitable denaturing method including physical, chemical or enzymatic means. One method of separating the nucleic acid strands involves heating the nucleic acid until it is predominately denatured (e.g., greater than 50%, 60%, 70%, 80%, 90% or 95% denatured). The heating conditions necessary for denaturing template nucleic acid will depend, e.g., on the buffer salt concentration and the length and nucleotide composition of the nucleic acids being denatured, but typically range from about 90° C. to about 105° C. for a time depending on features of the reaction such as temperature and the nucleic acid length. Denaturation is typically performed for about 30 sec to 4 min.

If the double-stranded nucleic acid is denatured by heat, the reaction mixture is allowed to cool to a temperature that promotes annealing of each primer to its target sequence on the mecA nucleic acid. The temperature for annealing is usually from about 35° C. to about 65° C. Annealing times can be from about 10 secs to about 1 min. The reaction mixture is then adjusted to a temperature at which the activity of the polymerase is promoted or optimized, i.e., a temperature sufficient for extension to occur from the annealed primer such that products complementary to the template nucleic acid are generated. The temperature should be sufficient to synthesize an extension product from each primer that is annealed to a nucleic acid template, but should not be so high as to denature an extension product from its complementary template (e.g., the temperature for extension generally ranges from about 40° to 80° C.). Extension times can be from about 10 secs to about 5 mins. PCR assays can employ nucleic acid such as DNA or RNA, including messenger RNA (mRNA). The template nucleic acid need not be purified; it may be a minor fraction of a complex mixture, such as *Staphylococcus* nucleic acid contained in human cells. DNA or RNA may be extracted from a biological sample such as nasal swabs, throat swabs, feces, dermal swabs, lymphoid tissue, cerebrospinal fluid, blood (and blood in blood culture bottles), sputum, bronchio-alveolar lavage, bronchial aspirates, lung tissue, and urine by routine techniques such as those described in *Diagnostic Molecular Microbiology: Principles and Applications* (Persing et al. (eds), 1993, American Society for Microbiology, Washington D.C.). Nucleic acids can be obtained from any number of sources, such as plasmids, or natural sources including bacteria, yeast, viruses, organelles, or higher organisms such as plants or animals.

The oligonucleotide primers are combined with PCR reagents under reaction conditions that induce primer extension. For example, extension reactions generally include 50 mM KCl, 10 mM Tris-HCl (pH 8.3), 1.5 mM $MgCl_2$, 0.001% (w/v) gelatin, 0.5-1.0 µg denatured template DNA, 50 pmoles of each oligonucleotide primer, 2.5 U of Taq polymerase, and 10% DMSO). The reactions usually contain 150 to 320 µM each of dATP, dCTP, dTTP, dGTP, or one or more analogs thereof.

The newly synthesized strands form a double-stranded molecule that can be used in the succeeding steps of the reaction. The steps of strand separation, annealing, and elongation can be repeated as often as needed to produce the desired quantity of amplification products corresponding to the target mecA nucleic acid molecule. The limiting factors in the reaction are the amounts of primers, thermostable enzyme, and nucleoside triphosphates present in the reaction. The cycling steps (i.e., denaturation, annealing, and extension) are preferably repeated at least once. For use in detection, the number of cycling steps will depend, e.g., on the nature of the sample. If the sample is a complex mixture of nucleic acids, more cycling steps will be required to amplify the target sequence sufficient for detection. Generally, the cycling steps are repeated at least about 20 times, but may be repeated as many as 40, 60, or even 100 times.

Fluorescence Resonance Energy Transfer (FRET)

FRET technology (see, for example, U.S. Pat. Nos. 4,996,143, 5,565,322, 5,849,489, and 6,162,603) is based on a concept that when a donor fluorescent moiety and a corresponding acceptor fluorescent moiety are positioned within a certain distance of each other, energy transfer takes place between the two fluorescent moieties that can be visualized or otherwise detected and/or quantitated. Two oligonucleotide probes, each containing a fluorescent moiety, can hybridize to an amplification product at particular positions determined by the complementarity of the oligonucleotide probes to the target nucleic acid sequence. Upon hybridization of the oligonucleotide probes to the amplification product at the appropriate positions, a FRET signal is generated. Hybridization temperatures can range from about 35° C. to about 65° C. for about 10 secs to about 1 min.

Fluorescent analysis can be carried out using, for example, a photon counting epifluorescent microscope system (containing the appropriate dichroic mirror and filters for monitoring fluorescent emission at the particular range), a photon counting photomultiplier system or a fluorometer. Excitation to initiate energy transfer can be carried out with an argon ion laser, a high intensity mercury (Hg) arc lamp, a fiber optic light source, or other high intensity light source appropriately filtered for excitation in the desired range.

As used herein with respect to donor and corresponding acceptor fluorescent moieties "corresponding" refers to an acceptor fluorescent moiety having an emission spectrum that overlaps the excitation spectrum of the donor fluorescent moiety. The wavelength maximum of the emission spectrum of the acceptor fluorescent moiety should be at least 100 nm greater than the wavelength maximum of the excitation spectrum of the donor fluorescent moiety. Accordingly, efficient non-radiative energy transfer can be produced therebetween.

Fluorescent donor and corresponding acceptor moieties are generally chosen for (a) high efficiency Förster energy transfer; (b) a large final Stokes shift (>100 nm); (c) shift of the emission as far as possible into the red portion of the visible spectrum (>600 nm); and (d) shift of the emission to a higher wavelength than the Raman water fluorescent emission produced by excitation at the donor excitation wavelength. For example, a donor fluorescent moiety can be chosen that has its excitation maximum near a laser line (for example, Helium-Cadmium 442 nm or Argon 488 nm), a high extinction coefficient, a high quantum yield, and a good overlap of its fluorescent emission with the excitation spectrum of the corresponding acceptor fluorescent moiety. A corresponding acceptor fluorescent moiety can be chosen that has a high extinction coefficient, a high quantum yield, a good overlap of its excitation with the emission of the donor fluorescent moiety, and emission in the red part of the visible spectrum (>600 nm).

Representative donor fluorescent moieties that can be used with various acceptor fluorescent moieties in FRET technology include fluorescein, Lucifer Yellow, B-phycoerythrin, 9-acridineisothiocyanate, Lucifer Yellow VS, 4-acetamido-4'-isothio-cyanatostilbene-2,2'-disulfonic acid, 7-diethylamino-3-(4'-isothiocyanatophenyl)-4-methylcoumarin, succinimdyl 1-pyrenebutyrate, and 4-acetamido-4'-isothiocyanatostilbene-2,2'-disulfonic acid derivatives. Representative acceptor fluorescent moieties, depending upon the donor fluorescent moiety used, include LC™-Red 640 (LightCycler™-Red 640-N-hydroxysuccinimide ester), LC™-RED 705 (LightCycler™-Red 705-Phosphoramidite), cuanine dyes such as CY5 and CY5.5, Lissamine rhodamine B sulfonyl chloride, tetramethyl rhodamine isothiocyanate, rhodamine x isothiocyanate, erythrosine isothiocyanate, fluorescein, diethylenetriamine pentaacetate or other chelates of Lanthanide ions (e.g., Europium, or Terbium). Donor and acceptor fluorescent moieties can be obtained, for example, from Molecular Probes (Junction City, Oreg.) or Sigma Chemical Co. (St. Louis, Mo.).

The donor and acceptor fluorescent moieties can be attached to the appropriate probe oligonucleotide via a linker arm. The length of each linker arm is important, as the linker arms will affect the distance between the donor and acceptor fluorescent moieties. The length of a linker arm for the purpose of the present invention is the distance in Angstroms (Å) from the nucleotide base to the fluorescent moiety. In general, a linker arm is from about 10 to about 25 Å. The linker arm may be of the kind described in WO 84/03285. WO 84/03285 also discloses methods for attaching linker arms to a particular nucleotide base, and also for attaching fluorescent moieties to a linker arm.

An acceptor fluorescent moiety such as LC™-RED 640 (LightCycler™-Red 640-N-hydroxysuccinimide ester) can be combined with C6-Phosphoramidites (available from ABI (Foster City, Calif.) or Glen Research (Sterling, Va.)) to produce, for example, LC™-RED 640 (LightCycler™-Red 640-Phomhoramidite). Frequently used linkers to couple a donor fluorescent moiety such as fluorescein to an oligonucleotide include thiourca linkers (FITC-derived, for example, fluorescein-CPG's from Glen Research or Chem-Gene (Ashland, Mass.)), amide-linkers (fluorescein-NHS-ester-derived, such as fluorescein-CPG from BioGenex (San Ramon, Cailf.)), or 3'-amino-CPG's that require coupling of a fluorescein-NHS-ester after oligonucleotide synthesis.

Detection of mecA-Containing *Stayhylococcus* spp.

Current phenotypic, culture-based methods require at least 48 hours and frequently longer to detect β-lactam resistance associated with the mecA gene. Furthermore, the phenotypic evaluation of mecA-associated resistance may lack sensitivity and specificity for some staphylococcal species, e.g., *S. lugdunensis*. The "gold standard" test is a traditional agar or broth dilution test with dilutions of antibiotics. These tests require 18 to 24 hours to perform. This in addition to the time required for isolation of the organism from clinical specimens, which may require an additional 24–48 hours.

A recent test, The Velogeneʊ Genomic Identification Assay for MRSA, uses cycling probe technology (CPT) to give a visual identification result in 90 minutes starting from a primary isolate. Velogene kits utilize a fluorescein labeled biotinylated DNA-RNA-DNA chimeric probe that binds to the complementary sequence of the mecA gene for MRSA. When the probe has hybridized with the target DNA, RNase H cleaves the RNA portion of the chimeric probe, which results in a fluorescein labeled fragment and a biotinylated fragment. The cleaved probe disassociates from the target DNA allowing the probe cleavage cycle to be repeated. At the end of a 25–30 minute CPT reaction, the intact probe is detected in an ELISA format using a streptavidin-coated microtiter plate with an anti-fluorescein horseradish peroxidase conjugate. If complementary mecA target sequences are present in the isolate, all the probe molecules are cleaved and the ELISA well remains clear. If no target is present, the intact probe is captured in the ELISA well and the well turns blue from the action of horseradish peroxidase on TMB. The Velogene assay requires more hands on time than the rapid PCR test and does not have the potential for testing directly from patient samples.

The invention provides an assay for detecting mecA-containing *Staphylococcus* spp. The LIGHTCYCLER™ PCR assay is the first automated, real-time system for the detection of *Staphylococcus* mecA nucleic acid. The system is rapid (2–3 hours total sample preparation and analytical time), is sensitive (detects ≧10 copies of mecA DNA/sample), specific (detects mecA DNA target exclusively), and has a wide dynamic linear range of $10^1$ to $10^7$ copies of mecA/sample. By using commercially available real-time PCR instrumentation (e.g., LIGHTCYCLER™, Roche Molecular Biochemicals, Indianapolis, Ind.), PCR amplification and detection of the amplification product can be combined in a single closed cuvette with dramatically reduced cycling time. Since detection occurs concurrently with amplification, the real-time PCR methods obviate the need for manipulation of the amplification product, and diminish the risk of cross-contamination between amplification products. Real-time PCR greatly reduces turn-around time and is an attractive alternative to conventional PCR techniques in the clinical laboratory.

The present invention provides methods for detecting the presence or absence of one or more mecA-containing *Staphylococcus* spp. in a biological sample from an individual. Methods provided by the invention avoid problems of sample contamination, false negatives, and false positives. The methods include performing at least one cycling step that includes amplifying a portion of a mecA nucleic acid molecule from a sample using a pair of mecA primers, respectively. Each of the mecA primers anneals to a target within or adjacent to a mecA nucleic acid molecule such that at least a portion of each amplification product contains nucleic acid sequence corresponding to mecA. More importantly, the amplification product should contain the nucleic acid sequences that are complementary to the mecA probes. The mecA amplification product is produced provided that mecA nucleic acid is present. Each cycling step further includes contacting the sample with a pair of mecA probes. According to the invention, one member of each pair of the mecA probes is labeled with a donor fluorescent moiety and the other is labeled with a corresponding acceptor fluorescent moiety. The presence or absence of FRET between the donor fluorescent moiety of the first mecA probe and the corresponding acceptor fluorescent moiety of the second mecA probe is detected upon hybridization of the mecA probes to the mecA amplification product.

Each cycling step includes an amplification step and a hybridization step, and each cycling step is usually followed by a FRET detecting step. Multiple cycling steps are performed, preferably in a thermocycler. Methods of the invention can be performed using the mecA primer and probe sets to detect the presence of mecA-containing *Staphylococcus* spp. As used herein, "mecA-containing *Staphylococcus* spp." refers to *Staphylococcus* species that contain mecA nucleic acid sequences.

As used herein, "amplifying" refers to the process of synthesizing nucleic acid molecules that are complementary to one or both strands of a template nucleic acid molecule (e.g., mecA nucleic acid molecules). Amplifying a nucleic acid molecule typically includes denaturing the template nucleic acid, annealing primers to the template nucleic acid at a temperature that is below the melting temperatures of the primers, and enzymatically elongating from the primers to generate an amplification product. Amplification typically requires the presence of deoxyribonucleoside triphosphates, a DNA polymerase enzyme (e.g., PLATINUM® TAQ (derived from recombinant Taq DNA polymerase by binding of a thermolabile inhibitor containing monoclonal antibodies to Taq DNA polymerase such that the inhibitor is denatured during the initial denaturation step of PCR and active Taq DNA polymerase is released into the reaction)) and an appropriate buffer and/or co-factors for optimal activity of the polymerase enzyme (e.g., $MgCl_2$ and/or KCl).

If amplification of mecA nucleic acid occurs and an amplification product is produced, the step of hybridizing results in a detectable signal based upon FRET between the members of the pair of probes. As used herein, "hybridizing" refers to the annealing of probes to an amplification product. Hybridization conditions typically include a temperature that is below the melting temperature of the probes but that avoids non-specific hybridization of the probes.

Generally, the presence of FRET indicates the presence of one or more mecA-containing *Staphylococcus* spp. in the sample, and the absence of FRET indicates the absence of mecA-containing *Staphylococcus* spp. in the sample. Inadequate specimen collection, transportation delays, inappropriate transportation conditions, or use of certain collection swabs (calcium alginate or aluminum shaft) are all conditions that can affect the success and/or accuracy of a test result, however. Using the methods disclosed herein, detection of FRET within 45 cycling steps is indicative of a *Staphylococcus* infection.

Representative biological samples that can be used in practicing the methods of the invention include nasal swabs, throat swabs, feces, dermal swabs, lymphoid tissue, cerebrospinal fluid, blood (and blood in blood culture bottles), sputum, bronchio-alveolar lavage, bronchial aspirates, lung tissue, and urine. Collection and storage methods of biological samples are known to those of skill in the art. Biological samples can be processed (e.g., by nucleic acid extraction methods and/or kits known in the art) to release *Staphylococcus* nucleic acid or in some cases, the biological sample can be contacted directly with the PCR reaction components and the appropriate oligonucleotides.

Melting curve analysis is an additional step that can be included in a cycling profile. Melting curve analysis is based on the fact that a nucleic acid sequence melts at a characteristic temperature called the melting temperature (Tm), which is defined as the temperature at which half of the DNA duplexes have separated into single strands. The melting temperature of a DNA depends primarily upon its nucleotide composition. Thus, DNA molecules rich in G and C nucleotides have a higher Tm than those having an abundance of A and T nucleotides. By detecting the temperature at which the FRET signal is lost, the melting temperature of probes can be determined. Similarly, by detecting the temperature at which signal is generated, the annealing temperature of probes can be determined. The melting temperature(s) of the mecA probes from the respective amplification product can confirm the presence or absence of mecA-containing *Staphylococcus* spp. in the sample.

Within each thermocycler run, control samples are cycled as well. Positive control samples can amplify nucleic acid control template (e.g., a nucleic acid other than mecA) using, for example, control primers and control probes. Positive control samples can also amplify, for example, a plasmid construct containing a mecA nucleic acid molecule. Such a plasmid control can be amplified internally (e.g., within the sample) or in a separate sample run side-by-side with the patients' samples. Each thermocycler run should also include a negative control that, for example, lacks mecA template DNA. Such controls are indicators of the success or failure of the amplification, hybridization and/or FRET reaction. Therefore, control reactions can readily determine, for example, the ability of primers to anneal with sequence-specificity and to initiate elongation, as well as the ability of probes to hybridize with sequence-specificity and for FRET to occur.

In an embodiment, the methods of the invention include steps to avoid contamination. For example, an enzymatic method utilizing uracil-DNA glycosylase is described in U.S. Pat. Nos. 5,035,996, 5,683,896 and 5,945,313 to reduce or eliminate contamination between one thermocycler run and the next. In addition, standard laboratory containment practices and procedures are desirable when performing methods of the invention. Containment practices and procedures include, but are not limited to, separate work areas for different steps of a method, containment hoods, barrier filter pipette tips and dedicated air displacement pipettes. Consistent containment practices and procedures by personnel are necessary for accuracy in a diagnostic laboratory handling clinical samples.

Conventional PCR methods in conjunction with FRET technology can be used to practice the methods of the invention. In one embodiment, a LIGHTCYCLER™ instrument is used. A detailed description of the LIGHTCYCLER™ System and real-time and on-line monitoring of PCR can be found at on Roche's website. The following patent applications describe real-time PCR as used in the LIGHTCYCLER™ technology: WO 97/46707, WO 97/46714 and WO 97/46712. The LIGHTCYCLER™ instrument is a rapid thermal cycler combined with a microvolume fluorometer utilizing high quality optics. This rapid thermocycling technique uses thin glass cuvettes as reaction vessels. Heating and cooling of the reaction chamber are controlled by alternating heated and ambient air. Due to the low mass of air and the high ratio of surface area to volume of the cuvettes, very rapid temperature exchange rates can be achieved within the LIGHTCYCLER™ thermal chamber. Addition of selected fluorescent dyes to the reaction components allows the PCR to be monitored in real time and on-line. Furthermore, the cuvettes serve as an optical element for signal collection (similar to glass fiber optics), concentrating the signal at the tip of the cuvette. The effect is efficient illumination and fluorescent monitoring of microvolume samples.

The LIGHTCYCLER™ carousel that houses the cuvettes can be removed from the instrument. Therefore, samples can be loaded outside of the instrument (in a PCR Clean Room, for example). In addition, this feature allows for the sample carousel to be easily cleaned and sterilized. The fluorometer, as part of the LIGHTCYCLER™ apparatus, houses the light source. The emitted light is filtered and focused by an epi-illumination lens onto the top of the cuvette. Fluorescent light emitted from the sample is then focused by the same lens, passed through a dichroic mirror, filtered appropriately, and focused onto data-collecting photohybrids. The optical unit currently available in the LLGHTCYCLER™ instrument (Roche Molecular Biochemicals, Catalog No. 2 011 468) includes three band-pass filters (530 nm, 640 nm, and 710 nm), providing three-color detection and several fluorescence acquisition options. Data collection options include once per cycling step monitoring, fully continuous single-sample acquisition for melting curve analysis, continuous sampling (in which sampling frequency is dependent on sample number) and/or stepwise measurement of all samples after defined temperature interval.

The LIGHTCYCLER™ can be operated using a PC workstation and can utilize a Windows NT operating system. Signals from the samples are obtained as the machine positions the capillaries sequentially over the optical unit. The software can display the fluorescence signals in real-time immediately after each measurement. Fluorescent acquisition time is 10–100 milliseconds (msec). After each cycling step, a quantitative display of fluorescence vs. cycle number can be continually updated for all samples. The data generated can be stored for further analysis.

As an alternative to FRET, an amplification product can be detected using a double-stranded DNA binding dye such as a fluorescent DNA binding dye (e.g., SYBRGREEN® or SYBRGOLD® (Molecular Probes)). Upon interaction with the double-stranded nucleic acid, such fluorescent DNA binding dyes emit a fluorescence signal after excitation with light at a suitable wavelength. A double-stranded DNA binding dye such as a nucleic acid intercalating dye also can be used. When double-stranded DNA binding dyes are used, a melting curve analysis is usually performed for confirmation of the presence of the amplification product.

As described herein, amplification products also can be detected using labeled hybridization probes that take advantage of FRET technology. A common format of FRET technology utilizes two hybridization probes. Each probe can be labeled with a different fluorescent moiety and are generally designed to hybridize in close proximity to each other in a target DNA molecule (e.g., an amplification product). A donor fluorescent moiety, for example, fluorescein, is excited at 470 nm by the light source of the LIGHTCYCLER™ Instrument. During FRET, the fluorescein transfers its energy to an acceptor fluorescent moiety such as LC™-RED 640 (LightCycler™-Red 640-N-hydroxysuccinimide ester) or LC™-RED 705 (LightCycler™-Red 705-Phosnhoramidite). The acceptor fluorescent moiety then emits light of a longer wavelength, which is detected by the optical detection system of the LIGHTCYCLER™ instrument. Efficient FRET can only take place when the fluorescent moieties are in direct local proximity and when the emission spectrum of the donor fluorescent moiety overlaps with the absorption spectrum of the acceptor fluorescent moiety. The intensity of the emitted signal can be correlated with the number of original target DNA molecules (e.g., the number of copies of mecA).

Another FRET format utilizes TAQMAN® technology to detect the presence or absence of an amplification product, and hence, the presence or absence of mecA-containing *Staphylococcus* spp. TAQMAN® technology utilizes one single-stranded hybridization probe labeled with two fluorescent moieties. When a first fluorescent moiety is excited with light of a suitable wavelength, the absorbed energy is transferred to a second fluorescent moiety according to the principles of FRET. The second fluorescent moiety is generally a quencher molecule. During the annealing step of the PCR reaction, the labeled hybridization probe binds to the target DNA (i.e., the amplification product) and is degraded by the 5' to 3' exonuclease activity of the Taq Polymerase during the subsequent elongation phase. As a result, the excited fluorescent moiety and the quencher moiety become spatially separated from one another. As a consequence, upon excitation of the first fluorescent moiety in the absence of the quencher, the fluorescence emission from the first fluorescent moiety can be detected. By way of example, an ABI PRISM® 7700 Sequence Detection System (Applied Biosystems, Foster City, Calif.) uses TAQMAN® technology, and is suitable for performing the methods described herein for detecting mecA-containing *Staphylococcus* spp. Information on PCR amplification and detection using an ABI PRISM® 770 system can be found on Applied Biosystems' website.

Molecular beacons in conjunction with FRET also can be used to detect the presence of an amplification product using the real-time PCR methods of the invention. Molecular beacon technology uses a hybridization probe labeled with a first fluorescent moiety and a second fluorescent moiety. The second fluorescent moiety is generally a quencher, and the fluorescent labels are typically located at each end of the probe. Molecular beacon technology uses a probe oligonucleotide having sequences that permit secondary structure formation (e.g., a hairpin). As a result of secondary structure formation within the probe, both fluorescent moieties are in spatial proximity when the probe is in solution. After hybridization to the target nucleic acids (i.e., amplification products), the secondary structure of the probe is disrupted and the fluorescent moieties become separated from one another such that after excitation with light of a suitable wavelength, the emission of the first fluorescent moiety can be detected.

It is understood that the present invention is not limited by the configuration of one or more commercially available instruments.

Articles of Manufacture

The invention further provides for articles of manufacture to detect mecA-containing *Staphylococcus* spp. An article of manufacture according to the present invention can include primers and probes used to detect mecA-containing *Staphylococcus* spp., together with suitable packaging materials. Representative primers and probes for detection of mecA-containing *Staphylococcus* spp. are capable of hybridizing to mecA nucleic acid molecules. Methods of designing primers and probes are disclosed herein, and representative examples of primers and probes that amplify and hybridize to mecA nucleic acid molecules are provided.

Articles of manufacture of the invention also can include one or more fluorescent moieties for labeling the probes or, alternatively, the probes supplied with the kit can be labeled. For example, an article of manufacture may include a donor fluorescent moiety for labeling one of the mecA probes and an acceptor fluorescent moiety for labeling the other mecA probe. Examples of suitable FRET donor fluorescent moieties and corresponding acceptor fluorescent moieties are provided above.

Articles of manufacture of the invention also can contain a package insert or package label having instructions thereon for using the mecA primers and probes to detect *Staphylococcus* spp. in a sample. Articles of manufacture may additionally include reagents for carrying out the methods disclosed herein (e.g., buffers, polymerase enzymes, co-factors, or agents to prevent contamination). Such reagents may be specific for one of the commercially available instruments described herein.

The invention will be further described in the following examples, which do not limit the scope of the invention described in the claims.

EXAMPLES

Example 1

Oligonucleotide Primers and Probes

Primers and probes were designed using the OLIGO software (Molecular Biology Insights, Inc., Cascade, Oreg.). Primers were synthesized on a 0.2 μM scale by the Mayo Molecular Biology Core Facility (Rochester, Minn.). Probes were synthesized by TIB Molbiol LLC (Adelphia, N.J.), and were dissolved in TE' (10 mM Tris (pH 8.0), 0.1 mM EDTA)

to a final concentration of 20 μM. Sequences for primers and probes are shown in Table 1. The GenBank Accession number for the reference sequence used to design the primers and probes for each target is shown in Table 1.

TABLE 1

Primers and Probes for the Detection of *S. aureus*

| Gene Target | Gene Bank Accession # | Position (Product Size, bp) | Primer/ Probe Name | Sequence |
|---|---|---|---|---|
| mecA | AB033763 | 315 | mecA-F | 5'-AAA CTA CGG TAA CAT TGA TCG CAA C-3' (Forward Primer) (SEQ ID NO:1) |
| | | | mecA-R | 5'-TCT TGT ACC CAA TTT TGA TCC ATT T-3' (Reverse Primer) (SEQ ID NO:2) |
| | | | mecA-FL | 5'-GTG GAA TTG GCC AAT ACA GGA ACA GCA TA-3' (SEQ ID NO:3) |
| | | | mecA-RD | 5'-GAG ATA GGC ATC GTT CCA AAG AAT GTA-3' (SEQ ID NO:4) |

Primers were adjusted to 50 μM by measuring the $A_{260}$ of a 1/50 dilution (196 μl water+4 μl, Dilution Factor (DF) =50). The concentration was estimated by the following formula:

(μM found/50)×μl remaining)−μl remaining=water to add

Probes were dissolved in TE' to a concentration of 20 μM (supplied with the probes and resuspended according to manufacturer's instructions). The concentration of oligonucleotides and dye was double checked by UV absorption using the following equations from *Biochemica*, 1999,1: 5–8:

$$[dye] = \frac{A_{dye}}{E_{dye}} \quad [oligo] = \frac{A_{260} - \left(A_{260} \times \frac{E_{260(dye)}}{E_{dye}}\right)}{\frac{10^6}{nmol/A_{260}}}$$

| | Absorbance | | Emission |
|---|---|---|---|
| Dye | Abs max (nm) | $E_{dye}$ ($M^{-1}cm^{-1}$) | $E_{260(dye)}$ ($M^{-1}cm^{-1}$) | Max (nm) |
| Fluorescein | 494 | 68,000 | 2,000 | 524 |
| LC Red 640 | 622 | 110,000 | 31,000 | 638 |

Plasmid controls were produced by cloning the mecA product amplified by the mecA primers into the pCR® 2.1 TOPO® TA cloning vector (Invitrogen Corp., Carlsbad, Calif.). The recombinant vectors were transformed into chemically competent TOP10 *E. coli* cells. The correct recombinant plasmid was confirmed and purified with a Wizard MiniPrep (Promega Corp., Madison, Wiss.) Cleaning kit. The stock concentrations of the controls (in genomic equivalents) were determined. The plasmid containing the mecA insert was used to determine the analytical sensitivity of the assay. Plasmid concentration or the copy number of the gene target insert was determined with the following formula:

DS DNA, $A_{260}$ to molecules/μ

Given:
1. ($A_{260}$×Dilution Factor)/20=mg/ml =μg/μl DS DNA
   1 $A_{260}$ =50 μg/ml
   1 $A_{260}$ (50)=μg/ml
   1 $A_{260}$ (50)/1000=μg/μl
2. ($6.02×10^{23}$ molecules/mole)/($10^{12}$ pmole/mole)=$6.02×10^{11}$ molecules/pmole
3. Base pairs of DNA in molecule=N Then:

($A_{260}$×DF)/20 μg/μl×$10^6$ pg/μg×1 pmol/660 pg×1/N× $6.02×10^{11}$ molecules/pmole=molecules/μl Shortcut calculation:

(($A_{260}$×DF)/20)×($9.12×10^{14}$/N)=molecules/μl

Example 2

PCR Conditions

A mechanical method of shaking with small beads was used to lyse *staphylococcus* from colonies, blood or blood culture media. The advantages of mechanical lysis are speed, simplicity and low cost. The sensitivity was found to be less than 10 organisms per assay, suggesting adequate lysis.

*Staphylococcus* extraction buffer (SEB) (1 mM EDTA, 0.1 mM EGTA, 0.1 mM TRIS (pH 8.0)) was used when extracting nucleic acid from colonies to inhibit nucleases from the organism, especially *S. aureus* thermonuclease. *S. aureus* thermonuclease prefers calcium as a cofactor, and the EGTA in the buffer chelates calcium and inhibits the enzyme. EDTA was used to bind magnesium, which is the cofactor for most nucleases. The concentration of both chelators was low enough to have minimal effect on the PCR reaction without additional sample cleanup.

The extracted nucleic acid from a colony had a very high concentration of target DNA, so the potential for contamination was higher. When working with these types of samples, careful handling to contain the target nucleic acids was necessary.

For extraction of nucleic acids from culture, the following protocol was followed. 500 μl of SEB was added to a bead tube (FastPrep Lysing Matrix B, QBiogene, Inc. Catalog #6911-100). A portion of a bacterial colony was placed in the bead tube. The cap was replaced and the sample processed using the FastPrep instrument (Qbiogene, Inc.) for 30 seconds at speed setting 6.0, or the tube placed into a Disruptor Genie (Scientific Industries) for 60 seconds. The tube was centrifuged for 30 seconds at 12,000 to 20,000×g to pellet any particulate material. The upper supernatant was analyzed for mecA using the LIGHTCYCLER™ assay.

For extraction of nucleic acids from blood, blood culture media, and other specimens, the following method was used. The extraction was confirmed using the BD Bactec™PLUS+ Aerobic/F blood culture media. 500 μl blood or blood culture media was placed in a bead tube. Swabs were swirled in the bead tube with 500 μl SEB. The cap was replaced and the sample was processed as described above using the FastPrep or the Disruptor Genie. The tube was centrifuged for 30 seconds at 12,000 to 20,000×g. 200 µl was extracted using MagNAPure (Roche, Catalog 3 038 505). Other extraction methods did not perform well with the blood culture media. The extracted nucleic acid was analyzed for mecA by the LIGHTCYCLER™ assay.

For the LIGHTCYCLER™ assay, a 5 µl aliquot of extracted nucleic acid was added to 15 µl of LIGHTCYCLER™ Master Mix in each reaction capillary. A no-target control received 15 µl of LIGHTCYCLER™ Master Mix with 5 µl water.

LIGHTCYCLER™ Master Mix-mecA

| Ingredient | Stock | Final | µl |
| --- | --- | --- | --- |
| Water | — | — | 110 |
| MgCl$_2$ | 50 mM | 3 mM | 12 |
| FastStart Reagent[a] | 10 X | 1 X | 20 |
| Primer-F&R | 25 µM | 0.5 µM | 4 |
| Probe-FL | 20 µM | 0.2 µM | 2 |
| Probe-RD | 20 µM | 0.2 µM | 2 |
| Total volume | | | 150 |

[a]contains 1 mM Mg, PLATINUM ® TAQ, and dNTPs

The PCR reagents and specimen extract are centrifuged in the capillary to facilitate mixing. All capillaries are then sealed and amplified using the following protocol.

Quantification Settings:
 Channel Settings F2
 Experimental Protocol:
  Melt (1 cycle) Type: none
   95° C., 10 min, 20°/sec slope
  PCR(40 cycles) Type: Quantification
   95° C., 10 sec hold, 20° C./sec slope
   55° C., 10 sec hold, 20° C./sec slope, single acquisition
   72° C., 12 sec hold, 20° C./sec slope
  Melt (1 cycle) Type: Melting Curve
   95° C., 10 sec hold, 20° C./sec slope
   60° C., 0 sec hold, 2° C./sec slope
   45° C., 30 sec hold, 0.2° C./sec slope
   85° C., 0 sec hold, 0.2° C./sec slope, continuous acquisition
  Cool (1 cycle) Type: None
   40°, 30 sec hold, 20° C./sec slope Amplification of the mecA sequences using the mecA primers disclosed herein results in a 315 bp amplification product.

Example 3

Results, Assay Validation, and Quality Control

For the following control experiments, amplification was performed as described above in Examples 1 and 2.

Control experiments were performed to determine if the primers and probes described herein for detecting vancomycin-resistant enterococci cross-reacted with DNA from similar organisms or from organisms commonly found in the specimens. For the crossreactivity panels, the presence of microorganism DNA was initially confirmed by amplification of 16S rRNA and electrophoretic separation of the amplification product (Johnson, 1994, *Methods for General and Molecular Bacteriology*, American Society for Microbiology, Washington D.C.).

Respiratory Specificity Panel

| Sample | Organism | Source | mecA |
| --- | --- | --- | --- |
| R2 | Acinetobacter lwoffli | QC Strain | negative |
| R3 | Aeromonas hydrophilia | CAP-D-1-82 | negative |
| R4 | Bordetella bronchioseptica | patient isolate | negative |
| R5 | Bordetella holmesii | patient isolate | negative |
| R6 | Bordetella parapertussis | ATCC 15311 | negative |
| R7 | Bordetella pertussis | ATCC 9797 | negative |
| R8 | Campylobacter jejuni | CDC-AB2-C15-82 | negative |
| R10 | Corynebacterium (Archanobacterium) haemolyticum | patient isolate | negative |
| R11 | Corynebacterium dipheriae | SCB-25-86 | negative |
| R12 | Corynebacterium pseudodiptheriae | NY-4-88 | negative |
| R13 | Eseherichia coli | patient isolate | negative |
| R14 | Haemophilus influenza | ATCC 49766 | negative |
| R15 | Homo sapiens | MRC-5 cells | negative |
| R16 | Klebsiella oxytoca | patient isolate | negative |
| R17 | Klebsiella pneumoniae | patient isolate | negative |
| R18 | Legionella jordanis | ATCC 33623 | negative |
| R19 | Legionella pneumophila | ATCC 33152 | negative |
| R20 | Listeria monocytogenes | patient isolate | negative |
| R21 | Moraxella catarrhalis | patient isolate | negative |
| R22 | Morganella morganji | CAP-D-5-79 | negative |
| R23 | Mycoplasma pneumoniae | patient isolate | negative |
| R24 | Neiserria gonorrheae | patient isolate | negative |
| R25 | Neiserria meningitidis | patient isolate | negative |
| R26 | Proteus mirabilis | patient isolate | negative |
| P27 | Proteus vulgaris | patient isolate | negative |
| P28 | Pseudomonas aeruginosa | ATCC 27853 | negative |
| P29 | Pseudomonas cepacia | patient isolate | negative |
| R30 | Pseudomonas fluorescens | patient isolate | negative |
| R31 | Staphylococcus aureus | ATCC 25923 | negative |
| R32 | Staphylococcus epidermidis | patient isolate | negative |
| R33 | Stenotrophomonas maltophilia | SOB-33-77 | negative |
| R34 | Legionella micdadei | ATCC 33204 | negative |
| R35 | Citrobacter freundii | patient isolate | negative |
| R36 | Streptococcus pneumoniae | ATCC 49619 | negative |
| R37 | Bordetella bronchioseptica | ATCC 19395 | negative |
| R38 | Streptococcus pyogenes | patient isolate | negative |

Staphylococcus Specificity Panel

| Sample | Organism | Source | mecA |
| --- | --- | --- | --- |
| S1 | Staphylococcus aureus | ATCC 25923 | negative |
| S3 | Staphylococcus capitis ssp. capitis | ATCC 35661 | negative |
| S4 | Staphylococcus caprae | patient isolate | negative |
| S5 | Staphylococcus cohnii ssp. cohnii | ATCC 13509 | negative |
| S6 | Staphylococcus epidermidis | MK 214 | negative |
| S7 | Staphylococcus haemolyticus | patient isolate | negative |
| S8 | Staphylococcus hominis ssp. horminus | patient isolate | negative |
| S9 | Staphylococcus lugdunensis | patient isolate | negative |
| S10 | Staphylococcus saprophticus | CAP-D-11-88 | negative |
| S11 | Staphylococcus sciuri ssp. sciuri | ATCC 29060 | negative |
| S12 | Staphylococcus simulans | patient isolate | negative |
| S13 | Staphylococcus warneri | patient isolate | negative |
| S14 | Staphylococcus xylosus | ATCC 700404 | negative |
| S15 | Staphylococcus lentus | ATCC 700403 | negative |
| S16 | Rothia (Stomatococcus) mucilaginosa | patient isolate | negative |

The respiratory and *staphylococcus* specificity panels did not show cross-reactivity with the LIGHTCYCLER™ mecA assay.

In addition, control experiments were performed to determine if LIGHTCYCLER™ amplification from clinical samples produced a single amplification product. Amplification products were analyzed by 2% agarose gel electrophoresis. In positive clinical specimens, amplification using the LIGHTCYCLER™ protocol generated a single band at the expected size.

Additional control experiments were performed using dilutions of positive control plasmid to determine the sensitivity of the LIGHTCYCLER™ assay. Plasmid dilutions were as follows.

| Stock to dilute | μl stock | μl diluent | Copy/μl | Copy/5 μl |
|---|---|---|---|---|
| $2 \times 10^5$/μl | 100 | 900 | $2 \times 10^4$/μl | 100,000 |
| $2 \times 10^4$/μl | 100 | 900 | $2 \times 10^3$/μl | 10,000 |
| $2 \times 10^3$/μl | 100 | 900 | $2 \times 10^2$/μl | 1000 |
| $2 \times 10^2$/μl | 100 | 900 | $2 \times 10^1$/μl | 100 |
| $2 \times 10^1$/μl | 100 | 900 | 1/μl | 10 |

Data was plotted as the level of fluorescence detected relative to the cycle number for each dilution value. The slope of the standard curve was −3.269 with an r value=− 0.99. Using the formulas Exponential Amplification=$10^{(-1/slope)}$, and Efficiency=$10^{(-1/slope)} - 1$, the efficiency of the reaction was determined to be 1.02. The sensitivity of the LIGHTCYCLER™ reaction was less than 50 copies of target per 5 μl of sample. The efficiency of the reaction was >95%.

Further control experiments were performed to determine the sensitivity and specificity of the LIGHTCYCLER™ assay compared to culture-based methods. 50 patient isolates of MRSA and 50 methicillin sensitive S. aureus (MSSA) were randomly selected from patient's isolates of staphylococcus archived at the Mayo Clinic (Rochester, Minn.) and sensitivities were determined using standard agar dilution with oxacillin. The same isolates were grown on sheep blood agar plates at 37° C. overnight, lysed with 0.5 ml of SEB with 250 μl of 0.1 μM zirconium beads in a 2 ml screw cap polypropylene tube, and processed on a Fast Prep instrument at a speed setting of 6 for 30 secs. The tube was centrifuged for 1 min at 20,800×g, and 5 μl of the supernatant was analyzed by the LIGHTCYCLER™ assay described herein.

All MRSA samples were positive and all MSSA samples were negative by the LIGHTCYCLER™ mecA assay, thereby indicating that the LIGHTCYCLER™ assay provides 100% sensitivity and specificity. Initially, two isolates of MRSA (928 & 987) were negative by the LIGHTCYCLER™ mecA assay. The agar dilution susceptibilities were repeated and the isolates were both sensitive. It is presumed the mecA insertion sequence was lost upon freezing and subculture, which is not uncommon.

Control experiments also were performed to determine the precision (e.g., within-run, within-day, and between-day precision) of the LIGHTCYCLER™ assay. Within-run precision of the LIGHTCYCLER™ assay was evaluated by assaying 5 μl of a positive control dilution 10 times within the same amplification experiment. Within-day precision of the LIGHTCYCLER™ assay was evaluated by assaying 5 μl of a positive control dilution 10 times during a single day. Between-day precision of the LIGHTCYCLER™ assay was evaluated by assaying 5 μl of positive control dilution 10 times over a three-day period.

The average number of cycles at which FRET was detected in the within-run assays was 27.38±0.114; the average number of cycles at which FRET was detected in the within-day assays was 27.12±0.075; and the average number of cycles at which FRET was detected in the between-day precision was 27.16±0.072. The precision of the average crossing point measurement and the standard deviation was excellent.

Control experiments were performed to determine if the LIGHTCYCLER™ assay produces the same results using 2, 5 or 10 μl of the nucleic acid sample extracted from a patient's sample. Mixes were prepared for different target volumes essentially as described above, and 2 positive samples were tested at each volume. Similar results were obtained from patient specimens when 2 μl, 5 μl , or 10 μl of sample was used in the assay.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for detecting the presence or absence of *Staphylococcus* in a biological sample from an individual, said method comprising:

performing at least one cycling step, wherein a cycling step comprises an amplifying step and a hybridizing step, wherein said amplifying step comprises contacting said sample with a pair of mecA primers to produce a mecA amplification product if a *Staphylococcus* mecA nucleic acid molecule is present in said sample, wherein said pair of mecA primers comprises a first mecA primer and a second mecA primer, wherein said first mecA primer comprises the sequence 5'-AAACTACGG TAACATTGATCG CAAC-3' (SEQ ID NO:1), wherein said hybridizing step comprises contacting said sample with a pair of mecA probes, wherein the members of said pair of mecA probes hybridize to said amplification product within no more than five nucleotides of each other, wherein a first mecA probe of said pair of mecA probes is labeled with a donor fluorescent moiety and wherein a second mecA probe of said pair of mecA probes is labeled with a corresponding acceptor fluorescent moiety; and detecting the presence or absence of fluorescence resonance energy transfer (FRET) between said donor fluorescent moiety of said first mecA probe and said acceptor fluorescent moiety of said second mecA probe, wherein the presence of FRET is indicative of the presence of *Staphylococcus* in said biological sample, and wherein the absence of FRET is indicative of the absence of *Staphylococcus* in said biological sample.

2. The method of claim 1, wherein said second mecA primer comprises the sequence 5'-TCT TGTACC CAATTT TGATCC ATT T-3' (SEQ ID NO:2).

3. A method for detecting the presence or absence of *Staphylococcus* in a biological sample from an individual, said method comprising:

performing at least one cycling step, wherein a cycling step comprises an amplifying step and a hybridizing step, wherein said amplifying step comprises contacting said sample with a pair of mecA primers to produce a mecA amplification product if a *Staphylococcus* mecA nucleic acid molecule is present in said sample, wherein said pair of mecA primers comprises a first mecA primer and a second mecA primer, wherein said second mecA primer comprises the sequence 5'-TCT TGT ACC CAA TTT TGA TCC ATT T-3' (SEQ ID NO:2), wherein said hybridizing step comprises contacting said sample with a pair of mecA probes, wherein the members of said pair of mecA probes hybridize to said amplification product within no more than five nucleotides of each other, wherein a first mecA probe of said pair of mecA probes is labeled with a donor fluorescent moiety and wherein a second mecA probe of said pair of mecA probes is labeled with a corresponding acceptor fluorescent moiety; and detecting the presence or absence of fluorescence resonance energy transfer (FRET) between said donor fluorescent moiety of said first mecA probe and said acceptor fluorescent moiety of said second mecA probe, wherein the presence of FRET is indicative of the presence of *Staphylococcus* in said biological sample, and wherein the absence of FRET is indicative of the absence of *Staphylococcus* in said biological sample.

4. The method of claim 3, wherein said first mecA primer comprises the sequence 5'-AAA CTA CGG TAA CAT TGA TCG CAA C-3' (SEQ ID NO:1).

5. A method for detecting the presence or absence of *Staphylococcus* in a biological sample from an individual, said method comprising:

performing at least one cycling step, wherein a cycling step comprises an amplifying step and a hybridizing step, wherein said amplifying step comprises contacting said sample with a pair of mecA primers to produce a mecA amplification product if a *Staphylococcus* mecA nucleic acid molecule is present in said sample, wherein said hybridizing step comprises contacting said sample with a pair of mecA probes, wherein the members of said pair of mecA probes hybridize to said amplification product within no more than five nucleotides of each other, wherein a first mecA probe of said pair of mecA probes is labeled with a donor fluorescent moiety and wherein a second mecA probe of said pair of mecA probes is labeled with a corresponding acceptor fluorescent moiety, wherein said first mecA probe comprises the sequence 5'-GTG GAATTG GCC AATACAGGAACAGCATA-3' (SEQ ID NO:3); and detecting the presence or absence of fluorescence resonance energy transfer (FRET) between said donor fluorescent moiety of said first mecA probe and said acceptor fluorescent moiety of said second mecA probe, wherein the presence of FRET is indicative of the presence of *Staphylococcus* in said biological sample, and wherein the absence of FRET is indicative of the absence of *Staphylococcus* in said biological sample.

6. The method of claim 5, wherein said second mecA probe comprises the sequence 5'-GAGATAGGCATC GTT CCAAAGAAT GTA-3' (SEQ ID NO:4).

7. A method for detecting the presence or absence of *Staphylococcus* in a biological sample from an individual, said method comprising:

performing at least one cycling step, wherein a cycling step comprises an amplifying step and a hybridizing step, wherein said amplifying step comprises contacting said sample with a pair of mecA primers to produce a mecA amplification product if a *Staphylococcus* mecA nucleic acid molecule is present in said sample, wherein said hybridizing step comprises contacting said sample with a pair of mecA probes, wherein the members of said pair of mecA probes hybridize to said amplification product within no more than five nucleotides of each other, wherein a first mecA probe of said pair of mecA probes is labeled with a donor fluorescent moiety and wherein a second mecA probe of said pair of mecA probes is labeled with a corresponding acceptor fluorescent moiety, wherein said second mecA probe comprises the sequence 5'-GAG ATA GGC ATC GTT CCA AAG AAT GTA-3' (SEQ ID NO:4); and detecting the presence or absence of fluorescence resonance energy transfer (FRET) between said donor fluorescent moiety of said first mecA probe and said acceptor fluorescent moiety of said second mecA probe, wherein the presence of FRET is indicative of the presence of *Staphylococcus* in said biological sample, and wherein the absence of FRET is indicative of the absence of *Staphylococcus* in said biological sample.

8. The method of claim 7, wherein said first mecA probe comprises the sequence 5'-GTG GAATTG GCCAATA-CAGGAACAGCATA-3' (SEQ ID NO:3).

9. The method of claim 1, 3, 5, or 7, wherein the presence of said FRET within 45 cycling steps is indicative of the presence of a *Staphylococcus* infection in said individual.

10. The method of claim 1, 3, 5, or 7, wherein the presence of said FRET within 40 cycling steps is indicative of the presence of a *Staphylococcus* infection in said individual.

11. The method of claim 1, 3, 5, or 7, wherein the presence of said FRET within 30 cycling steps is indicative of the presence of a *Staphylococcus* infection in said individual.

12. The method of claim 1, 3, 5, or 7, wherein said cycling step is performed on a control sample.

13. The method of claim 12, wherein said control sample comprises said portion of said mecA nucleic acid molecule.

14. The method of claim 1, 3, 5, or 7, wherein said cycling step uses a pair of control primers and a pair of control probes, wherein said control primers and said control probes are other than said mecA primers and said mecA probes, wherein a control amplification product is produced if control template is present in said sample, wherein said control probes hybridize to said control amplification product.

15. The method of claim 1, 3, 5, or 7, wherein the members of said pair of probes hybridize within no more than two nucleotides of each other.

16. The method of claim 1, 3, 5, or 7, wherein the members of said pair of probes hybridize within no more than one nucleotide of each other.

17. The method of claim 1, 3, 5, or 7, wherein said donor fluorescent moiety is fluorescein.

18. The method of claim 1, 3, 5, or 7, wherein said detecting step comprises exciting said biological sample at a wavelength absorbed by said donor fluorescent moiety and visualizing and/or measuring the wavelength emitted by said acceptor fluorescent moiety.

19. The method of claim 1, 3, 5, or 7, wherein said detecting comprises quantitating said FRET.

20. The method of claim 1, 3, 5, or 7, wherein said detecting step is performed after each cycling step.

21. The method of claim 1, 3, 5, or 7, wherein said detecting step is performed in real time.

22. The method of claim 1, 3, 5, or 7, further comprising determining the melting temperature between one or both of said probe(s) and said amplification product, wherein said melting temperature confirms said presence or said absence of said mecA-containing *Staphylococcus*.

23. The method of claim 1, 3, 5, or 7, further comprising preventing amplification of a contaminant nucleic acid.

24. The method of claim 23, wherein said preventing comprises performing said amplifying step in the presence of uracil.

25. The method of claim 24, wherein said preventing further comprises treating said biological sample with uracil-DNA glycosylase prior to a first amplification step.

26. The method of claim 1, 3, 5, or 7, wherein said biological sample is selected from the group consisting of nasal swabs, throat swabs, feces, dermal swabs, lymphoid tissue, cerebrospinal fluid, blood, sputum, bronchio-alveolar lavage, bronchial aspirates, lung tissue, and urine.

27. A method for detecting the presence or absence of *Staphylococcus* in a biological sample from an individual, said method comprising:

performing at least one cycling step, wherein a cycling step comprises an amplifying step and a hybridizing step, wherein said amplifying step comprises contacting said sample with a pair of mecA primers to produce a mecA amplification product if a *Staphylococcus* mecA nucleic acid molecule is present in said sample, wherein said pair of mecA primers comprises a first mecA primer and a second mecA primer, wherein said first mecA primer comprises the sequence 5'-AAAC-TACGG TAACATTGATCG CAAC-3' (SEQ ID NO:1), wherein said hybridizing step comprises contacting said sample with a mecA probe, wherein said mecA probe is labeled with a donor fluorescent moiety and a corresponding acceptor fluorescent moiety; and detecting the presence or absence of fluorescence resonance energy transfer (FRET) between said donor fluorescent moiety and said acceptor fluorescent moiety of said mecA probe, wherein the presence or absence of FRET is indicative of the presence or absence of *Staphylococcus* in said sample.

28. The method of claim 27, wherein said second mecA primer comprises the sequence 5'-TCT TGT ACC CAA TTT TGA TCC ATT T-3' (SEQ ID NO:2).

29. A method for detecting the presence or absence of *Staphylococcus* in a biological sample from an individual, said method comprising:

performing at least one cycling step, wherein a cycling step comprises an amplifying step and a hybridizing step, wherein said amplifying step comprises contacting said sample with a pair of mecA primers to produce a mecA amplification product if a *Staphylococcus* mecA nucleic acid molecule is present in said sample, wherein said pair of mecA primers comprises a first mecA primer and a second mecA primer, wherein said second mecA primer comprises the sequence 5'-TCT TGT ACC CAA TTT TGA TCC ATT T-3' (SEQ ID NO:2), wherein said hybridizing step comprises contacting said sample with a mecA probe, wherein said mecA probe is labeled with a donor fluorescent moiety and a corresponding acceptor fluorescent moiety; and detecting the presence or absence of fluorescence resonance energy transfer (FRET) between said donor fluorescent moiety and said acceptor fluorescent moiety of said mecA probe, wherein the presence or absence of FRET is indicative of the presence or absence of *Staphylococcus* in said sample.

30. The method of claim 29, wherein said first mecA primer comprises the sequence 5'-AAA CTA CGG TAA CAT TGA TCG CAA C-3' (SEQ ID NO:1).

31. A method for detecting the presence or absence of *Staphylococcus* in a biological sample from an individual, said method comprising:

performing at least one cycling step, wherein a cycling step comprises an amplifying step and a hybridizing step, wherein said amplifying step comprises contacting said sample with a pair of mecA primers to produce a mecA amplification product if a *Staphylococcus* mecA nucleic acid molecule is present in said sample, wherein said hybridizing step comprises contacting said sample with a mecA probe, wherein said mecA probe is labeled with a donor fluorescent moiety and a corresponding acceptor fluorescent moiety, wherein said mecA probe comprises a sequence selected from the group consisting of 5'-GTG GAA TTG GCC AAT ACA GGAACA GCATA-3' (SEQ ID NO:3) and 5'-GAG ATA GGC ATC GTT CCAAAG AAT GTA-3' (SEQ ID NO:4); and detecting the presence or absence of fluorescence resonance energy transfer (FRET) between said donor fluorescent moiety and said acceptor fluorescent moiety of said mecA probe, wherein the presence or absence of FRET is indicative of the presence or absence of *Staphylococcus* in said sample.

32. The method of claim 31, wherein said first and second mecA primers comprise the sequences 5'-AAA CTA CGG TAA CAT TGA TCG CAA C-3' (SEQ ID NO:1) and 5'-TCT TGT ACC CAA TTT TGA TCC ATT T-3' (SEQ ID NO:2), respectively.

33. The method of claim 27, 29, or 31, wherein said amplification employs a polymerase enzyme having 5' to 3' exonuclease activity.

34. The method of claim 27, 29, or 31, wherein said donor and acceptor fluorescent moieties are within no more than 5 nucleotides of each other on said probe.

35. The method of claim 34, wherein said acceptor fluorescent moiety is a quencher.

36. The method of claim 27, 29, or 31, wherein said probe comprises a nucleic acid sequence that permits secondary structure formation, wherein said secondary structure formation results in spatial proximity between said donor and said acceptor fluorescent moiety.

37. The method of claim 36, wherein said acceptor fluorescent moiety is a quencher.

38. A method for detecting the presence or absence of *Staphylococcus* in a biological sample from an individual, said method comprising:

performing at least one cycling step, wherein a cycling step comprises an amplifying step and a dye-binding step, wherein said amplifying step comprises contacting said sample with a pair of mecA primers to produce a mecA amplification product if a *Staphylococcus* mecA nucleic acid molecule is present in said sample, wherein said pair of mecA primers comprises a first mecA primer and a second mecA primer, wherein said first mecA primer comprises the sequence 5'-AAAC-TACGG TAACAT TGATCG CAAC-3' (SEQ ID NO:1), wherein said dye-binding step comprises contacting said mecA amplification product with a nucleic acid binding dye; and detecting the presence or absence of binding of said nucleic acid binding dye to said amplification product, wherein the presence of binding is indicative of the presence of *Staphylococcus* in said sample, and wherein the absence of binding is indicative of the absence of *Staphylococcus* in said sample.

39. The method of claim 38, wherein said second mecA primer comprises the sequence 5'-TCT TGT ACC CAA TTT TGA TCC ATT T-3' (SEQ ID NO:2).

40. A method for detecting the presence or absence of *Staphylococcus* in a biological sample from an individual, said method comprising:

performing at least one cycling step, wherein a cycling step comprises an amplifying step and a dye-binding step, wherein said amplifying step comprises contacting said sample with a pair of mecA primers to produce a mecA amplification product if a *Staphylococcus* mecA nucleic acid molecule is present in said sample, wherein said pair of mecA primers comprises a first mecA primer and a second mecA primer, wherein said second mecA primer comprises the sequence 5'-TCT TGT ACC CAA TTT TGA TCC ATT T-3' (SEQ ID NO:2), wherein said dye-binding step comprises contacting said mecA amplification product with a nucleic acid binding dye; and detecting the presence or absence of binding of said nucleic acid binding dye to said amplification product, wherein the presence of binding is indicative of the presence of *Staphylococcus* in said sample, and wherein the absence of binding is indicative of the absence of *Staphylococcus* in said sample.

41. The method of claim 40, wherein said first mecA primer comprises the sequence 5'-AAA CTA CGG TAA CAT TGA TCG CAA C-3' (SEQ ID NO:1).

42. The method of claim 38 or 40, wherein said nucleic acid binding dye is ethidium bromide.

43. The method of claim 38 or 40, further comprising determining the melting temperature between said amplification product and said nucleic acid binding dye, wherein said melting temperature confirms said presence or absence of said mecA-containing *Staphylococcus*.

* * * * *

SEQUENCE LISTING

<160> NUMBER OF SEQ ID NOS: 4

<210> SEQ ID NO 1
<211> LENGTH: 25
<212> TYPE: DNA
<213> ORGANISM: Artificial Sequence
<220> FEATURE:
<223> OTHER INFORMATION: Oligonucleotide

<400> SEQUENCE: 1
aaactacggt aacattgatc gcaac                        25

<210> SEQ ID NO 2
<211> LENGTH: 25

-continued

```
<212> TYPE: DNA
<213> ORGANISM: Artificial Sequence
<220> FEATURE:
<223> OTHER INFORMATION: Oligonucleotide

<400> SEQUENCE: 2
tcttgtaccc aattttgatc cattt                                              25

<210> SEQ ID NO 3
<211> LENGTH: 29
<212> TYPE: DNA
<213> ORGANISM: Artificial Sequence
<220> FEATURE:
<223> OTHER INFORMATION: Oligonucleotide

<400> SEQUENCE: 3
gtggaattgg ccaatacagg aacagcata                                          29

<210> SEQ ID NO 4
<211> LENGTH: 27
<212> TYPE: DNA
<213> ORGANISM: Artificial Sequence
<220> FEATURE:
<223> OTHER INFORMATION: Oligonucleotide

<400> SEQUENCE: 4
gagataggca tcgttccaaa gaatgta                                            27
```